United States Patent [19]

Zheng et al.

[11] Patent Number: 6,028,207
[45] Date of Patent: Feb. 22, 2000

[54] BONE RESORPTION INHIBITION/ OSTEOGENESIS PROMOTION COMPOUND

[75] Inventors: Hu Zheng; Lingling Weng, both of Chengdu, China

[73] Assignees: Iskra Industry Co., Ltd., Tokyo, Japan; Institute of Pharmacology, West China University of Medical Sciences, Chengdu, China

[21] Appl. No.: 08/888,108

[22] Filed: Jul. 3, 1997

Related U.S. Application Data

[62] Division of application No. 08/338,505, Mar. 1, 1995, Pat. No. 5,760,214.

[51] Int. Cl.$^7$ .................................................. C07C 49/543
[52] U.S. Cl. ......................... 552/203; 552/205; 552/201
[58] Field of Search ..................................... 552/203, 205

[56] References Cited

U.S. PATENT DOCUMENTS

| | | | |
|---|---|---|---|
| 2,997,471 | 8/1961 | Cheney et al. | 260/247.2 |
| 4,925,833 | 5/1990 | McNamara et al. | 514/152 |
| 5,183,815 | 2/1993 | Saari et al. | 514/172 |
| 5,698,542 | 12/1997 | Zheng et al. | 514/152 |

FOREIGN PATENT DOCUMENTS

| | | |
|---|---|---|
| 62-26256 | 2/1987 | Japan . |
| 2-36145 | 2/1990 | Japan . |
| 4-352795 | 2/1992 | Japan . |

*Primary Examiner*—Jose' G. Dees
*Assistant Examiner*—Barbara Badio
*Attorney, Agent, or Firm*—Foley & Lardner

[57] ABSTRACT

A compound represented by the following formula (I):

$$X-Y-Z \qquad (I)$$

where Y is represented by the following formulae:

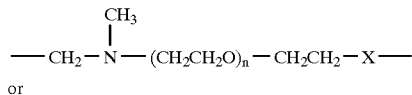

(IV)

or

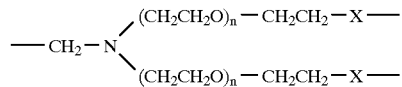

(V)

X is a monovalent group of a tetracycline type compounds and Z is a monovalent group of a steroid type compound such as estrogen.

The compound can concentrate on the bone tissue and has bone resorption inhibition/ossification promotion functions.

10 Claims, 6 Drawing Sheets

FIG. IC
FIG. ID
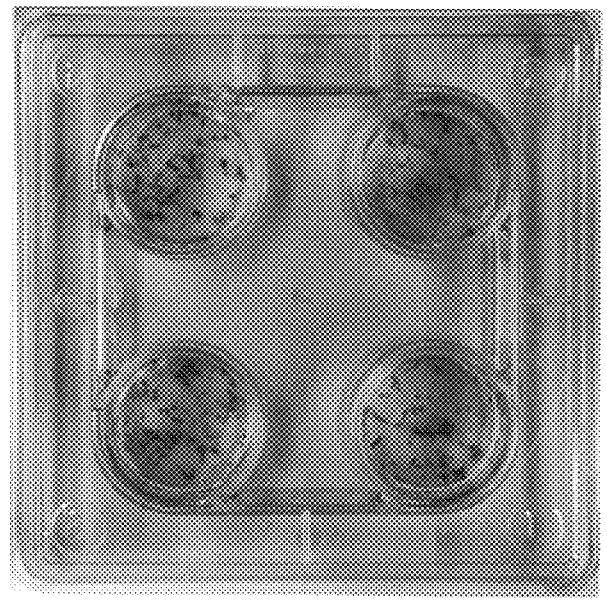

BONE RESORPTION INHIBITION/OSTEOGENESIS PROMOTION COMPOUND

This application is a division of U.S. application Ser. No. 08/338,505, filed Mar. 1, 1995, now U.S. Pat. No. 5,760,214.

TECHNICAL FIELD

This invention relates to compounds having novel bone resorption inhibition/osteogenesis promotion functions.

BACKGROUND ART

Normal retention of bones is accomplished by the balance of bone resorption and osteogenesis, and when bone resorption is promoted, bone components are dissolved and decrease, resulting in bone diseases such as osteoporosis. It is known that sex hormones such as estrogen have the function of suppressing bone resorption, and are therefore used as prophylactics and remedies for osteoporosis in Europe and America. Nonetheless, it has not yet been confirmed that these hormones concentrate on the bones, and the possibility of carcinogenesis resulting from single administration of these hormones cannot be denied.

On the other hand, tetracycline type antibiotics have a property such that they concentrate on the bones, but they have neither the bone resorption inhibition function nor the ossification function. Only U.S. Pat. No. 4,925,833 describes that tetracycline promotes the synthesis of bone proteins in the experiments of a cell level. Though the synthesis of the bone proteins is necessary for osteogenesis, the synthesis of the bone proteins alone cannot promote osteogenesis.

Materials which have the osteogenesis promotion function and which can be used as the prophylactics and remedies for bone diseases have not yet been known to this date.

Accordingly, the present invention contemplates to provide a remedy for bone diseases, which has a bone resorption inhibition function as well as osteogenesis function, preferably synergistically, and can concentrate on the bones.

DISCLOSURE OF THE INVENTION

The inventors of the present invention have conducted various studies so as to solve the problems described above and have found out that the compounds which are obtained by causing covalent bond between a tetracycline type antibiotic and a steroid type hormone such as estrogen by a linker has an osteogenesis function in addition to a bone resorption inhibition function and moreover, can concentrate on the bones, and have thus completed the present invention.

Accordingly, the present invention provides a bone resorption inhibitor/osteogenesis promoter expressed by the formula (I):

where X is a monovalent group represented by the following formula (II):

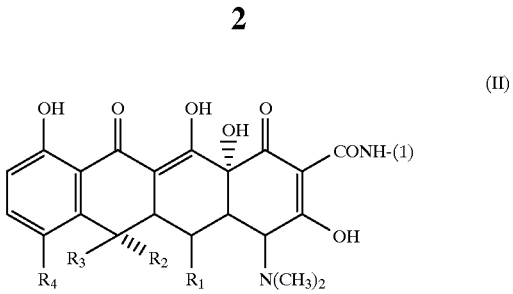

(where $R_1$ is hydrogen or a hydroxyl group, $R_2$ is hydrogen or a hydroxyl group, $R_3$ is hydrogen or a methyl group and $R_4$ is hydrogen, halogen or a dimethylamino group);

Y is a divalent or trivalent group represented by the following formula (III), (IV) or (V):

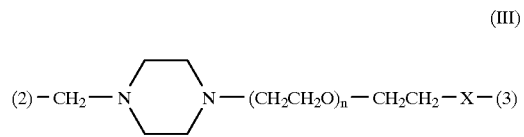

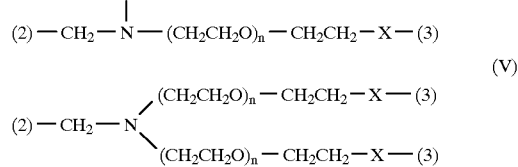

(where n is 0 to 4, and —X— is a direct bond, —O— or —NH—); and

Z is a monovalent group formed by removing hydrogen or a hydroxyl group from a compound represented by the following formula (VI):

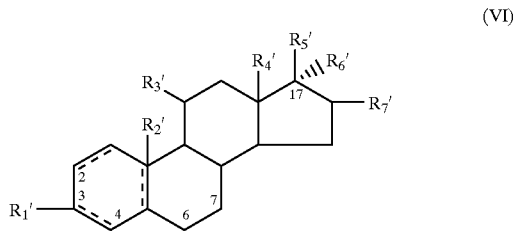

(where $R_1'$ is HO— or O=; $R_2'$ is a hydrogen atom or a methyl group; $R_3'$ is a hydrogen atom, a phenyl group or a substituted phenyl group; $R_4'$ is a methyl group or an ethyl group; $R_5'$ is a hydroxyl group, a ketone group or an acetyl group; $R_6'$ is hydrogen, a hydroxyl group, a methyl group, an ethynyl group or a prophynyl group; or $R_5'$ at and $R_6'$ together form =O; $R_7'$ is hydrogen, a hydroxyl group or =O; or $R_6'$ and $R_7'$ are together bonded to oxygens of a 2,2-dioxypropyl group, and symbol $\overline{\cdots}$ represents a single bond or a double bond), whereby this bond group exists at the 2-position, 3-position, 4-position, 6-position, 7-position or 17-position, or at the phenyl group bonded to the 11-position, (1) of the formula (II) and (2) of the formulas (III) to (V) are directly connected, and (3) of the formulas (III) to (V) and any of the bond groups of the formula (VI) are directly bonded].

In the formula (II) described above, the halogen is, for example, fluorine, chlorine, bromine or iodine, and is preferably chlorine.

BRIEF DESCRIPTION OF THE DRAWINGS

FIGS. 1 to 3 show the results when the same experiment is repeatedly carried out three times.

BEST MODE FOR CARRYING OUT THE INVENTION

Figure 1A:
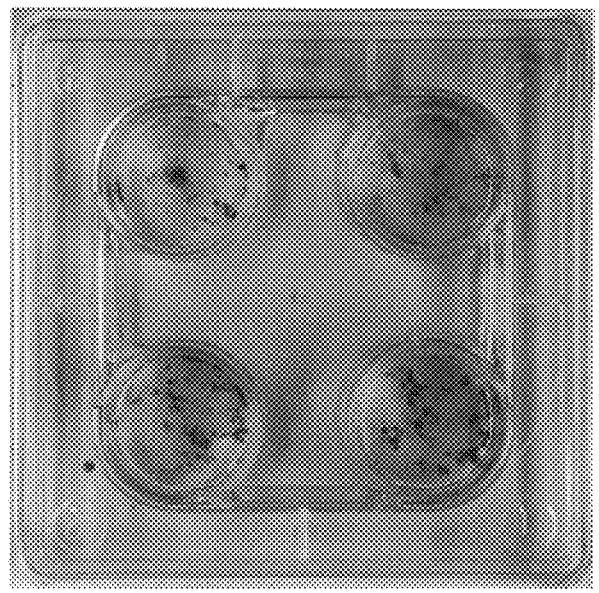
FIG. 1 is a photograph showing the result of Experiment No. 3.

Examples of the monovalent group of the formula (II) which is a moiety of the compound of the formula (I) as the active ingredient of the pharmaceutical of the present invention are as follows:

Formula (II-I):

Monovalent group of tetracycline represented by the formula (II-I) (where, in the formula (II), $R_1$ is hydrogen, $R_2$ is a hydroxyl group, $R_3$ is a methyl group and $R_4$ is hydrogen):

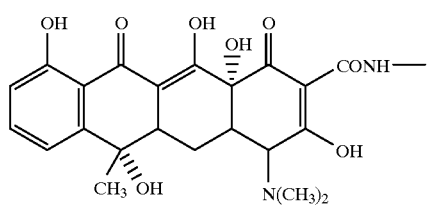
(II-1)

Formula (II-2):

Monovalent group of terramycin represented by the formula (II-2) (where, in the formula (II), $R_1$ is a hydroxyl group, $R_2$ is a hydroxyl group, $R_3$ is a methyl group and $R_4$ is a methyl group):

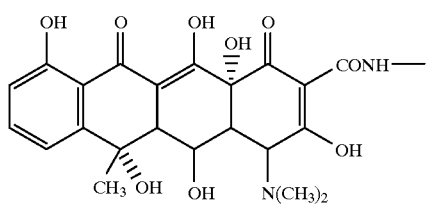
(II-2)

Formula (II-3):

Monovalent group of chlorotetracycline represented by the formula (II-3) (where, in the formula (II), $R_1$ is hydrogen, $R_2$ is a hydroxyl group, $R_3$ is a methyl group and $R_4$ is chlorine):

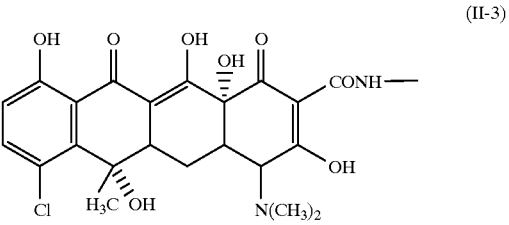
(II-3)

Formula (II-4):

Monovalent group of deoxytetracycline represented by the formula (II-4) (where, in the formula (II), $R_1$ is a hydroxyl group, $R_2$ is hydrogen, $R_3$ is a methyl group and $R_4$ is hydrogen):

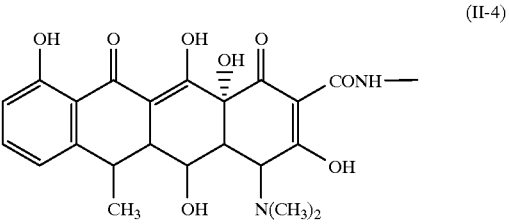
(II-4)

Formula (II-5):

Monovalent group of aminotetracycline represented by the formula (II-5) (where, in the formula (II), $R_1$ is hydrogen, $R_2$ is hydrogen, $R_3$ is hydrogen and $R_4$ is a dimethylamino group):

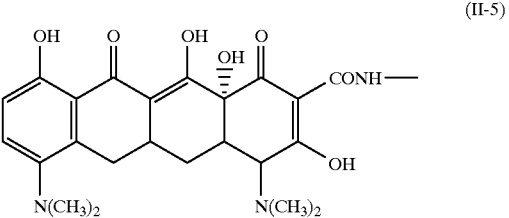
(II-5)

Examples of the monovalent groups of the compound of the formula (VI) which is a moiety of the compound of the formula (I) as the active ingredient of the pharmaceutical of the present invention are as follows.

Formula (VI-1):

Monovalent group of estron represented by the formula (VI-1) (where, in the formula (VI), $R_5'$ and $R_6'$ together form $=O$ and $R_7'$ is hydrogen):

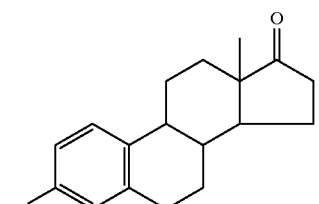
(VI-1)

Formula (VI-2):

Monovalent group of estradiol represented by the formula (VI-2) (where, in the formula (I), $R_5'$ is a hydroxyl group, $R_6'$ is hydrogen and $R_7'$ is hydrogen):

(VI-2)

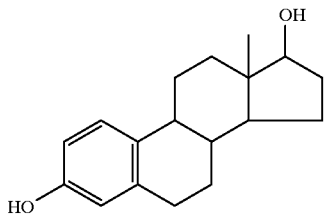

Formula (VI-3):

Monovalent group of estroalkynol represented by the formula (VI-3) (where, in the formula (VI), $R_5'$ is a hydroxyl group, $R_6'$ is an ethynyl group and $R_7'$ is hydrogen):

(VI-3)

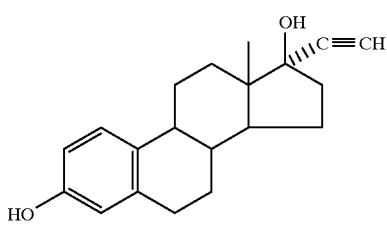

Formula (VI-4):

Monovalent group of estriol represented by the formula (VI-4) (where, in the formula (VI), $R_5'$ is a hydroxyl group, $R_6'$ is hydrogen and $R_7'$ is a hydroxyl group):

(VI-4)

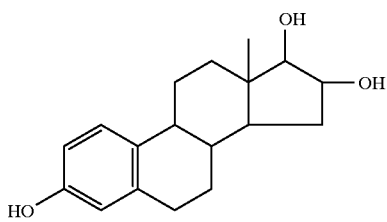

The bond group of the compounds of the formulas (VI) to (VI-4) described above exists at their 3-position, 6-position or 17-position. The The compound (VI) can further be those monovalent groups which are obtained by removing hydrogen or the hydroxyl group from the following compounds:

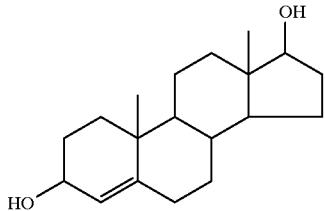

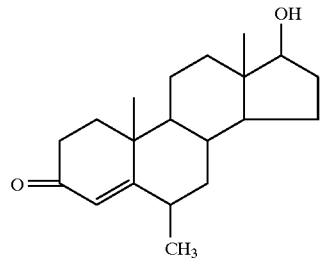

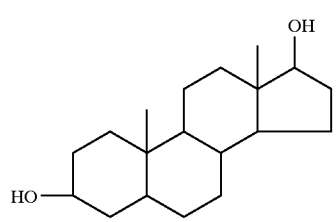

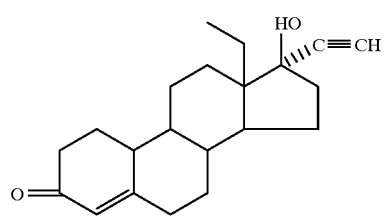

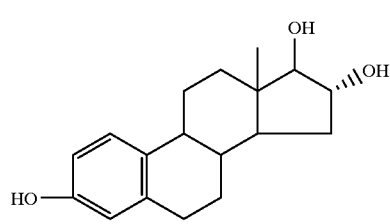

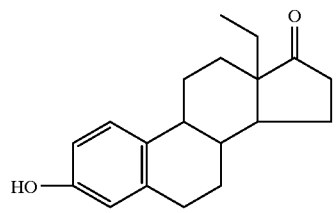

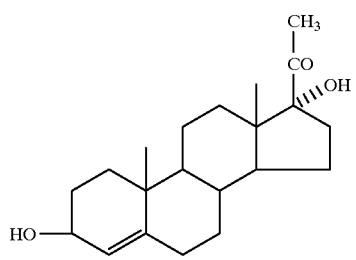
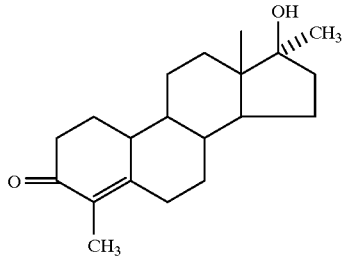
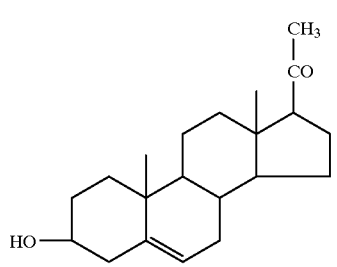
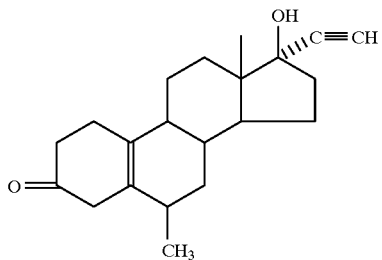
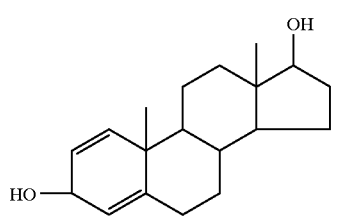
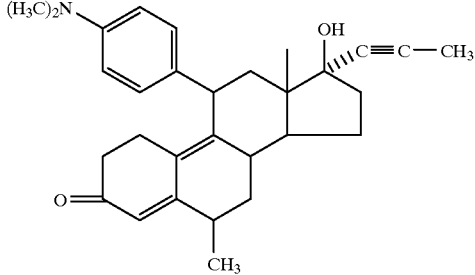
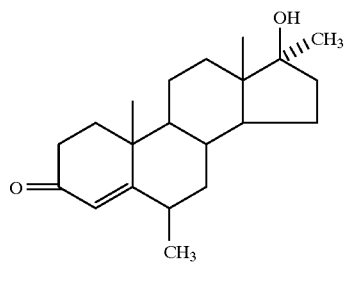
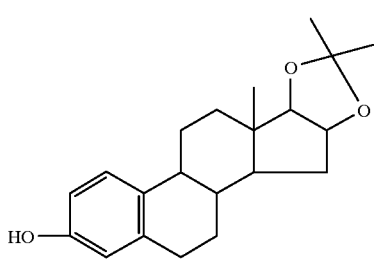
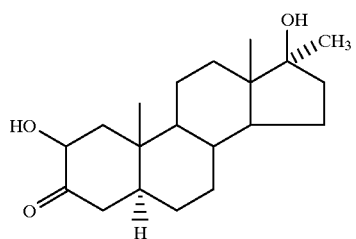
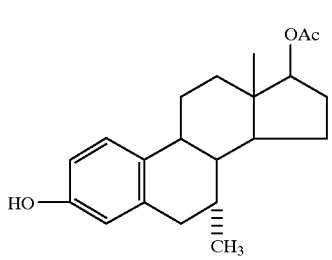

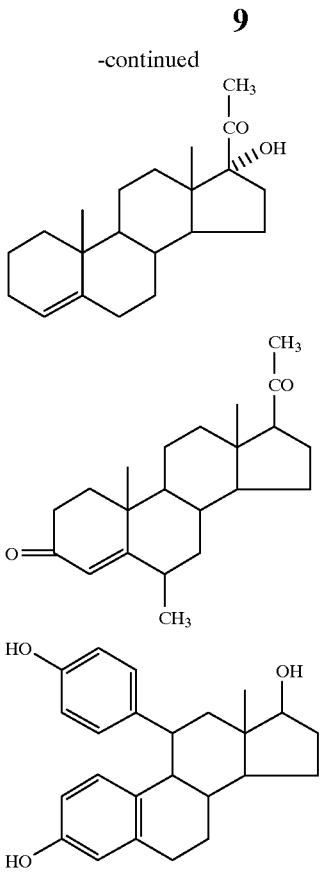

Accordingly, the active ingredient of the pharmaceutical of the present invention can be expressed by the following formulas, for example:

[II-1]-[III]-(3) [VI-1] (numeral in the parenthesis ( ) represents the position of the bond group of the group of the formula [VI-1]: hereinafter the same); [II-1]-[III]-(6) [VI-1], [II-1]-[III]-(17) [VI-1], [II-1]-[III]-(3) [VI-2], [II-1]-[III]-(6) [VI-2], [II-1]-[III]-(17) [VI-2], [II-1]-[III]-(3) [VI-3], [II-1]-[III]-(6) [VI-3], [II-1]-[III]-(17) [VI-3], [II-1]-[III]-(3) [VI-4], [II-1]-[III]-(6) [VI-4], [II-1]-[III]-(17) [VI-4],

[II-1]-[IV]-(3) [VI-1], [II-1]-[IV]-(6) [VI-1], [II-1]-[IV]-(17) [VI-1], [II-1]-[IV]-(3) [VI-2], [II-1]-[IV]-(6) [VI-2], [II-1]-[IV]-(17) [VI-2], [II-1]-[IV]-(3) [VI-3], [II-1]-[IV]-(6) [VI-3], [II-1]-[IV]-(17) [VI-3], [II-1]-[IV]-(3) [VI-4], [II-1]-[IV]-(6) [VI-4], [II-1]-[IV]-(17) [VI-4],

[II-1]-[V]-(3) [VI-1], [II-1]-[V]-(6) [VI-1], [II-1]-[V]-(17) [VI-1], [II-1]-[V]-(3) [VI-2], [II-1]-[V]-(6) [VI-2], [II-1]-[V]-(17) [VI-2], [II-1]-[V]-(3) [VI-3], [II-1]-[V]-(6) [VI-3], [II-1]-[V]-(17) [VI-3], [II-1]-[V]-(3) [VI-4], [II-1]-[V]-(6) [VI-4], [II-1]-[V]-(17) [VI-4],

[II-2]-[III]-(3) [VI-1], [II-2]-[III]-(6) [VI-1], [II-2]-[III]-(17) [VI-1], [II-2]-[III]-(3) [VI-2], [II-2]-[III]-(6) [VI-2], [II-2]-[III]-(17) [VI-2], [II-2]-[III]-(3) [VI-3], [II-2]-[III]-(6) [VI-3], [II-2]-[III]-(17) [VI-3], [II-2]-[III]-(3) [VI-4], [II-2]-[III]-(6) [VI-4], [II-2]-[III]-(17) [VI-4],

[II-2]-[IV]-(3) [VI-1], [II-2]-[IV]-(6) [VI-1], [II-2]-[IV]-(17) [VI-1], [II-2]-[IV]-(3) [VI-2], [II-2]-[IV]-(6) [VI-2], [II-2]-[IV]-(17) [VI-2], [II-2]-[IV]-(3) [VI-3], [II-2]-[IV]-(6) [VI-3], [II-2]-[IV]-(17) [VI-3], [II-2]-[IV]-(3) [VI-4], [II-2]-[IV]-(6) [VI-4], [II-2]-[IV]-(17) [VI-4],

[II-2]-[V]-(3) [VI-1], [II-2]-[V]-(6) [VI-1], [II-2]-[V]-(17) [VI-1], [II-2]-[V]-(3) [VI-2], [II-2]-[V]-(6) [VI-2], [II-2]-[V]-(17) [VI-2], [II-2]-[V]-(3) [VI-3], [II-2]-[V]-(6) [VI-3], [II-2]-[V]-(17) [VI-3], [II-2]-[V]-(3) [VI-4], [II-2]-[V]-(6) [VI-4], [II-2]-[V]-(17) [VI-4],

[II-3]-[III]-(3) [VI-1], [II-3]-[III]-(6) [VI-1], [II-3]-[III]-(17) [VI-1], [II-3]-[III]-(3) [VI-2], [II-3]-[III]-(6) [VI-2], [II-3]-[III]-(17) [VI-2], [II-3]-[III]-(3) [VI-3], [II-3]-[III]-(6) [VI-3], [II-3]-[III]-(17) [VI-3], [II-3]-[III]-(3) [VI-4], [II-3]-[III]-(6) [VI-4], [II-3]-[III]-(17) [VI-4],

[II-3]-[IV]-(3) [VI-1], [II-3]-[IV]-(6) [VI-1], [II-3]-[IV]-(17) [VI-1], [II-3]-[IV]-(3) [VI-2], [II-3]-[IV]-(6) [VI-2], [II-3]-[IV]-(17) [VI-2], [II-3]-[IV]-(3) [VI-3], [II-3]-[IV]-(6) [VI-3], [II-3]-[IV]-(17) [VI-3], [II-3]-[IV]-(3) [VI-4], [II-3]-[IV]-(6) [VI-4], [II-3]-[IV]-(17) [VI-4],

[II-3]-[V]-(3) [VI-1], [II-3]-[V]-(6) [VI-1], [II-3]-[V]-(17) [VI-1], [II-3]-[V]-(3) [VI-2], [II-3]-[V]-(6) [VI-2], [II-3]-[V]-(17) [VI-2], [II-3]-[V]-(3) [VI-3], [II-3]-[V]-(6) [VI-3], [II-3]-[V]-(17) [VI-3], [II-3]-[V]-(3) [VI-4], [II-3]-[V]-(6) [VI-4], [II-3]-[V]-(17) [VI-4],

[II-4]-[III]-(3) [VI-1], [II-4]-[III]-(6) [VI-1], [II-4]-[III]-(17) [VI-1], [II-4]-[III]-(3) [VI-2], [II-4]-[III]-(6) [VI-2], [II-4]-[III]-(17) [VI-2], [II-4]-[III]-(3) [VI-3], [II-4]-[III]-(6) [VI-3], [II-4]-[III]-(17) [VI-3], [II-4]-[III]-(3) [VI-4], [II-4]-[III]-(6) [VI-4], [II-4]-[III]-(17) [VI-4],

[II-4]-[IV]-(3) [VI-1], [II-4]-[IV]-(6) [VI-1], [II-4]-[IV]-(17) [VI-1], [II-4]-[IV]-(3) [VI-2], [II-4]-[IV]-(6) [VI-2], [II-4]-[IV]-(17) [VI-2], [II-4]-[IV]-(3) [VI-3], [II-4]-[IV]-(6) [VI-3], [II-4]-[IV]-(17) [VI-3]$_1$, [II-4]-[IV]-(3) [VI-4], [II-4]-[IV]-(6) [VI-4], [II-4]-[IV]-(17) [VI-4],

[II-4]-[V]-(3) [VI-1], [II-4]-[V]-(6) [VI-1], [II-4]-[V]-(17) [VI-1], [II-4]-[V]-(3) [VI-2], [II-4]-[V]-(6) [VI-2], [II-4]-[V]-(17) [VI-2], [II-4]-[V]-(3) [VI-3], [II-4]-[V]-(6) [VI-3], [II-4]-[V]-(17) [VI-3], [II-4]-[V]-(3) [VI-4], [II-4]-[V]-(6) [VI-4], [II-4]-[V]-(17) [VI-4],

[II-5]-[III]-(3) [VI-1], [II-5]-[III]-(6) [VI-1], [II-5]-[III]-(17) [VI-1], [II-5]-[III]-(3) [VI-2], [II-5]-[III]-(6) [VI-2], [II-5]-[III]-(17) [VI-2], [II-5]-[III]-(3) [VI-3], [II-5]-[III]-(6) [VI-3], [II-5]-[III]-(17) [VI-3], [II-5]-[III]-(3) [VI-4], [II-5]-[III]-(6) [VI-4], [II-5]-[III]-(17) [VI-4],

[II-5]-[IV]-(3) [VI-1], [II-5]-[IV]-(6) [VI-1], [II-5]-[IV]-(17) [VI-1], [II-5]-[IV]-(3) [VI-2], [II-5]-[IV]-(6) [VI-2], [II-5]-[IV]-(17) [VI-2], [II-5]-[IV]-(3) [VI-3], [II-5]-[IV]-(6) [VI-3], [II-5]-[IV]-(17) [VI-3], [II-5]-[IV]-(3) [VI-4], [II-5]-[IV]-(6) [VI-4], [II-5]-[IV]-(17) [VI-4],

[II-5]-[V]-(3) [VI-1], [II-5]-[V]-(6) [VI-1], [II-5]-[V]-(17) [VI-1], [II-5]-[V]-(3) [VI-2], [II-5]-[V]-(6) [VI-2], [II-5]-[V]-(17) [VI-2], [II-5]-[V]-(3) [VI-3], [II-5]-[V]-(6) [VI-3], [II-5]-[V]-(17) [VI-3], [II-5]-[V]-(3) [VI-4], [II-5]-[V]-(6) [VI-4], [II-5]-[V]-(17) [VI-4].

The compounds per se described above can be prepared by the known methods. For example, the linker represented by the formulas (III) to (V) is first bonded to the steroid compound represented by the formula (VI), and then the resulting bond product is bonded to the tetracycline type material.

Bonding of the linker of the formulas (III) to (V) to the 3-position of the steroid compound of the formula (VI) is carried out in accordance with the following reaction formula, for example:

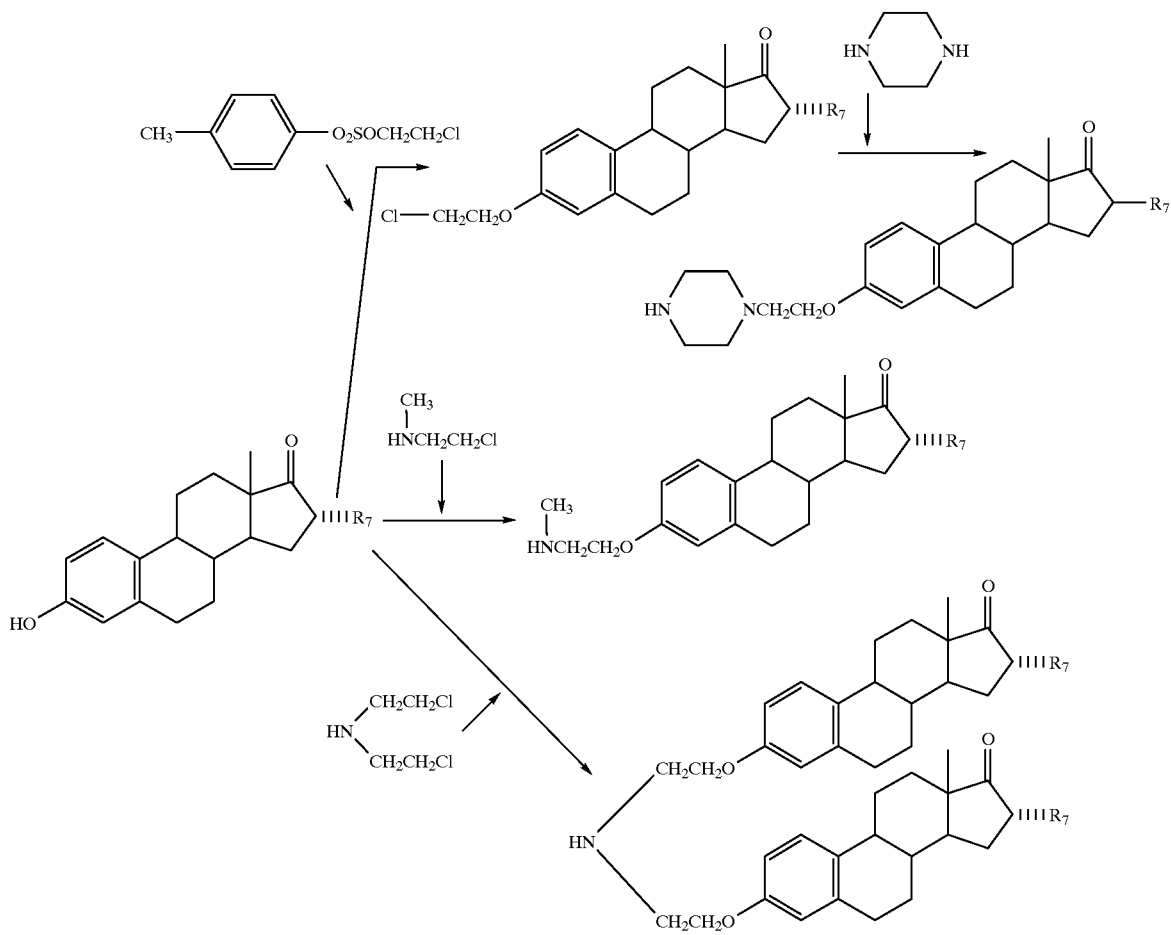
Further, the compound in which $R_5'$ is a hydroxyl group and $R_6'$ is hydrogen or an ethynyl group can be obtained by the following reaction, for example:
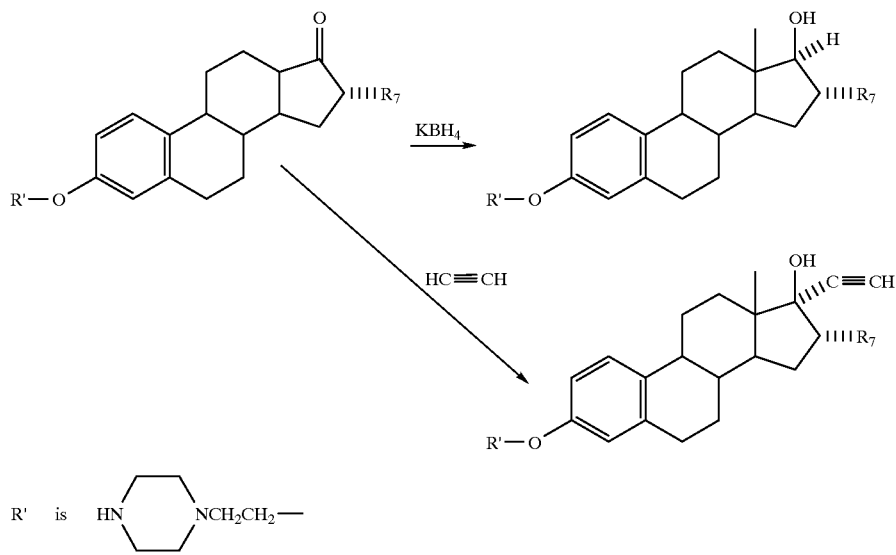

-continued or

To bond the linker of the formulas (III) to (V) to the 6-position of the steroid compound represented by the formula (VI), an =O group is first introduced into the 6-position of the steroid compound and then, the following reaction may be carried out:

so forth. They can be prepared in a customary manner. The liquid preparation, for example, can be prepared by dissolving or suspending the active ingredient of the present invention in an appropriate medium such as an aqueous buffer, or the like. The powder preparation can be prepared

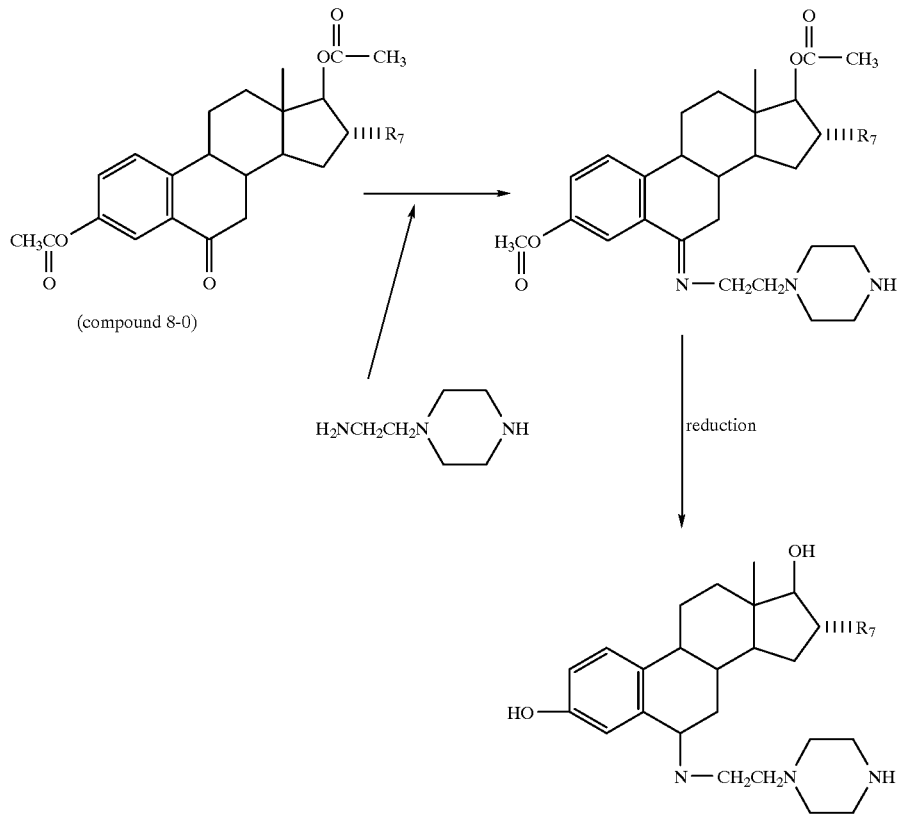

Next, the tetracycline compound can be bonded to the reaction product between the linker and the steroid compound by cross-linking the N atom of the linker with the N atom of the amide group of the tetracycline compound by formaldehyde.

The pharmaceutical according to the present invention can be dosed by peroral or parenteral administration such as phleboclysis, hyperdermic injection, intramuscular injection, intra-abdominal injection, and so forth. An effective daily dosage to man is from 0.2 to 200 mg in peroral administration and from 0.1 to 100 mg in parenteral administration. The compound of the present invention has extremely low toxicity, and an $LD_{50}$ in peroral administration of the compound 1 prepared in Example 1, for example, in mice is about 143 mg/kg.

The pharmaceutical of the present invention can take customary forms of preparations in accordance with the route of administration. In the case of peroral administration, for example, the pharmaceutical can take the forms of a capsule, a tablet, a granule, powder, a liquid preparation, and by mixing the active ingredient of the present invention with a powdery filler such as a starch, e.g. corn starch, and/or a saccharide such as lactose.

The tablet is prepared by mixing the active ingredient with the filler, such as the filler described above, and a binder such as starch paste, and compressing the mixture by a tableting machine. The granule can be prepared by mixing the active ingredient with the filler, the binder, etc., kneading the mixture with a liquid such as water and/or glycerine, passing the resulting product through a sieve to granulate it and drying the resulting granules. The capsule can be prepared by encapsulating powder or granule described above in a capsule having a suitable size.

The parenteral dosages can be prepared by dissolving or suspending the active ingredient in physiological saline solution or a buffer such as a phosphoric acid buffer, for example. The parenteral dosages may be freeze-dry products which are to be dissolved or suspended before use, and supports for freeze-drying may be saccharides such as lactose, or customary freeze-dry supports.

EXAMPLES

Hereinafter, concrete examples of the compounds according to the present invention will be described. However, the primary scope of the present invention is not limited to these examples.

Synthesis Example 1

Synthesis of 1-1.3-chloroethoxy-17-oxyestra-1,3,5 (10)-trien (Compound 1-1):

A NaOH solution was added to a toluene solution prepared by mixing 27.1 g of estrone, 22.2 g of 3-chloroethoxy-17-oxyestra-1,3,5 (10)-trien and a small amount of triethylaniline chloride. After a pH was adjusted to about 10, the reaction was carried out for 4 hours and the solvent was evaporated. The solid matter was recrystallized from alcohol, and a compound (1-1, $R_7$=H) was obtained. The yield was 79%. m.p.=86 to 88° C. elementary analysis: C 72.40, H 43, Cl 10.71

Synthesis of 1-2.N-[17-oxy-estra-1,3,5 (10)-trien-3oxyethyl]piperazine (Compound 1-2):

7.8 g of the compound (1-1) described above, 46.6 g of anhydrous piperazine and 120 ml of dimethyl formamide (DMF) were reacted at 80 to 100° C. for 5 hours. After DMF was evaporated and removed, the resulting solid matter was again recrystallized from alcohol and acetone so as to obtain a white crystalline compound (VI). The yield was 85%. m.p.=140 to 142° C. elementary analysis: C 75.10, H 9.20, N 7.40

Synthesis of 1-3.N-4-[17-oxy-estra-1,3,5 (10)-trien-3-oxyethyl]-piperazine-1-methylene-tetracycline (Compound 1-3):

3.8 g of the compound (1-2) described above, 0.03 g of metaformaldehyde and 15 ml of isopropanol were reacted at 40° C. for 2 hours. After 3.5 g of tetracycline was added, the mixture was stirred and reacted for 5 hours. After the reaction was completed, the reaction product was filtrated and was washed with isopropanol and ethyl ether. Thereafter, a yellow solid matter (compound 1-3) was obtained ($R_1$=$R_4$=H, $R_2$=OH, $R_3$=$CH_3$). The yield was 95%. m.p.=160° C. (dec) elementary analysis: C 67.21, H 7.12, N 6.67

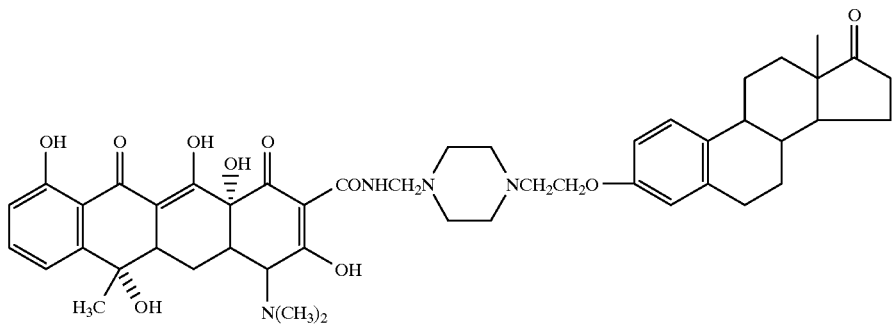

Synthesis Example 2

2-1. Synthesis of 2-1.N-[17β-hydroxy-estra-1,3,5 (10)-trien-3-oxyethyl]piperazine (Compound 2-1):

3.8 g of the compound (1-2) of Example 1 was dissolved in methyl alcohol. After 0.5 g of potassium borohydrate was added under an alkaline condition, the reaction mixture was reacted under heating and turning flow for 3 hours. The reaction solution was neutralized by an acid and methyl alcohol was evaporated. The resulting solid component was recrystallized from alcohol. Finally, a white crystal (compound 2-1, $R_7$=H) was obtained. The yield was 91%. m.p.=141 to 142° C. elementary analysis: C 75.21, H 9.23, N 7.14

2-2. Synthesis of N-4-[17β-hydroxy-estra-1,3,5 (10)-trien-3-oxyethyl]-piperazine-1-methylenetetracycline (Compound 2-2):

3.84 g of the compound (2-1) described above, 0.03 g of metaformaldehyde and 20 ml of isopropanol were reacted at 40° C. for 2 hours. After 3.5 g of tetracycline was added, the reaction mixture was stirred and reacted for 5 hours. After the reaction was completed, the reaction product was filtrated and was washed with isopropanol and ethyl ether. Thereafter, a pale yellow solid matter (compound 2-2) ($R_1$=$R_4$=H, $R_2$=OH, $R_3$=$CH_3$) was obtained. The yield was 95%. m.p.=165° C. (dec) elementary analysis: C 67.30, H 7.34, N 6.54

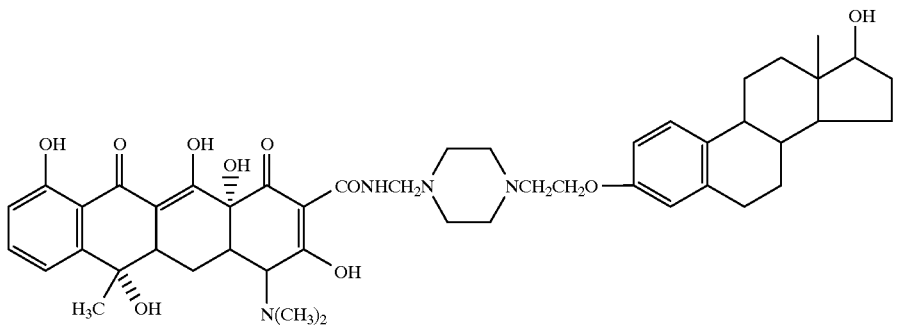

Synthesis Example 3

Synthesis of N-4-[17β-hydroxy-estra-1,3,5 (10)-trien-3-oxyethyl]-1-piperazine-1-methylene-oxytetracycline (Compound 3-1):

3.8 g of the compound of Example 2 (2-1), 0.03 g of metaformaldehyde and 20 ml of isopropanol were reacted at 40° C. for 2 hours. After 3.5 g of tetramycine was added, the reaction mixture was stirred and reacted for 5 hours. After the reaction was completed, the treatment was carried out in the same way as in Example 1–3, and a pale yellow solid matter (compound 3) ($R_1=R_2=OH$, $R_3=CH_3$, $R_4=H$) was obtained. The yield was 93%. m.p.=171° C. (dec) elementary analysis: C 65.62, H 7.10, N 6.67

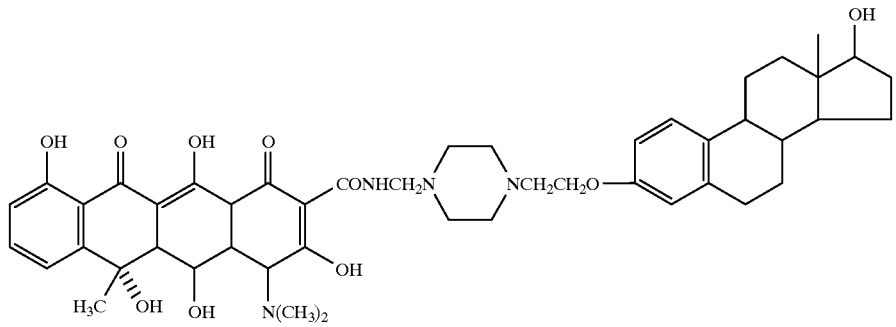

Synthesis Example 4

4-1. Synthesis of bis-N,N-[17-oxy-estra-1,3,5 (10)-trien-3-oxyethyl]amine (Compound 4-1)

A NaOH solution was added to a mixture of 3.6 g of mastagen chloride, 12 g of estron, 4 g of triethyl aniline, water and toluene with stirring. After the mixed solution was subjected to turning flow for 5 hours, the solvent was evaporated. The solid content was recrystallized from alcohol, and the intended product was obtained. The yield was 72%. m.p.=256 to 259° C. elementary analysis: C 78.50, H 8.60, N 2.31

4-2. Synthesis of bis-N,N-[17-oxy-estra-1,3,5 (10)-trien-3-oxyethyl] aminomethylene-tetracycline (Compound 4-2):

6.1 g of the compound (4-1) described above, 0.03 g of metaformaldehyde and 20 ml of isopropanol were reacted at 40° C. for 2 hours. After 3.5 g of tetracycline was added, the reaction mixture was stirred and reacted for 8 hours. After the reaction was completed, a pale yellow solid matter (compound 4-2) ($R_1=R_4=H$, $R_2=OH$, $R_3=CH_3$) was obtained. The yield was 68%. m.p.=183° C. (dec) elementary analysis: C 71.10, H 7.21, N 3.89

The structure was represented by the following molecular formula:

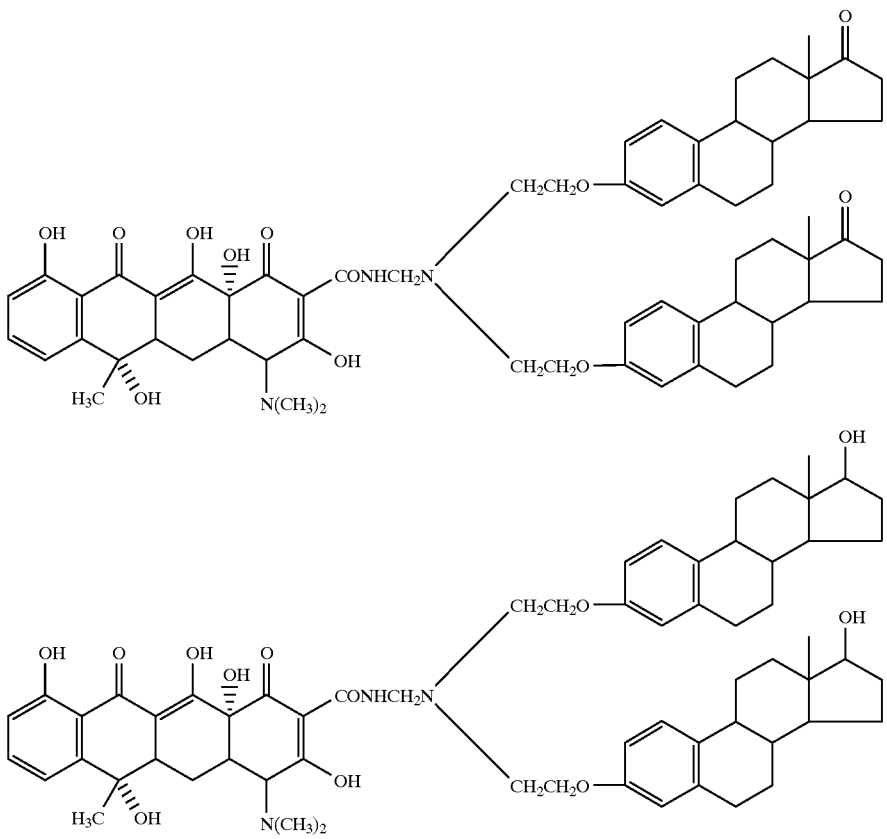

Synthesis Example 5

5-1. Synthesis of bis-N,N-[17β-hydroxy-estra-1,3,5 (10)-trien-3-oxyethyl]amine (Compound 5-1):

Methyl alcohol was added to 6.1 g of the compound (4-1) described above, and after 0.5 g of potassium borohydrate was added under an alkaline condition, the reaction was carried out under turning flow for 5 hours. Next, the reaction solution was neutralized by an acid and methyl alcohol was evaporated. The solid matter was refined in an acetone solution and an alcohol solution. Estron-17-ketone in the resulting compound (4-1) was reduced to a white product of -17β-hydroxyl group. The yield was 82%. m.p.=193 to 197° C. elementary analysis: C 78.41, H 8.51, N 2.33

5-2. Synthesis of bis-N,N-[17β-hydroxy-estra-1,3,5 (10)-trien-3-oxyethyl]aminomethylene-tetracycline (Compound 5-2):

5.4 g of the compound (5-1) described above, 0.03 g of metaformaldehyde and 20 ml of isopropanol were reacted at 40° C. for 2 hours. After 3.5 g of tetracycline was added, the reaction mixture was stirred and reacted for 8 hours. After the reaction was completed, a pale yellow solid matter (compound 5-2) ($R_1=R_4=H$, $R_2=OH$, $R_3=CH_3$) was obtained in the same way as in Example 1–3. The yield was 94%. m.p.=171° C. (dec) elementary analysis: C 71.02, H 7.02, N 3.98

The structure was represented by the following molecular formula:

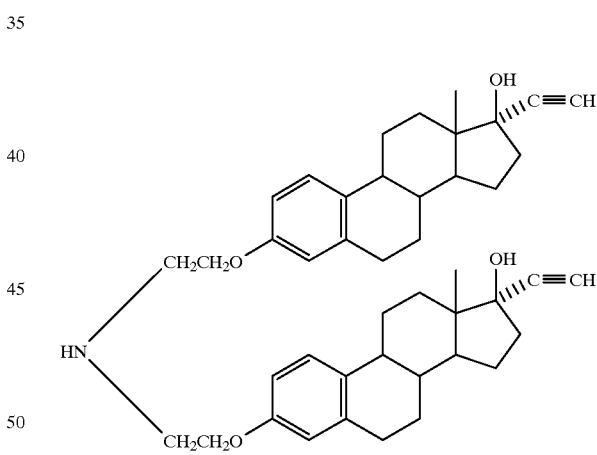

Synthesis Example 6

6-1. Synthesis of bis-N,N-[17β-hydroxy-17α-ethynyl-estra-1,3,5 (10)-trien-3-oxyethyl]amine (Compound 6-1):

6.1 g of the compound (4-1) of Example 4 was dissolved in 100 ml of tetrahydrofuran and 1.0 g of potassium hydroxide powder, and the mixture was completely reacted at 0° C. with vigorous stirring by introducing an acetylene gas. The reaction mixture was neutralized to pH 4 by an acid and the solvent was evaporated. The reaction product was then washed with water and was dried. It was further recrystallized from alcohol and chloroform, and a white solid matter (6-1) was obtained. The yield was 78%. m.p.=201 to 205° C. elementary analysis: C 79.21, H 8.58, N 2.18

The structure was expressed by the following molecular formula:

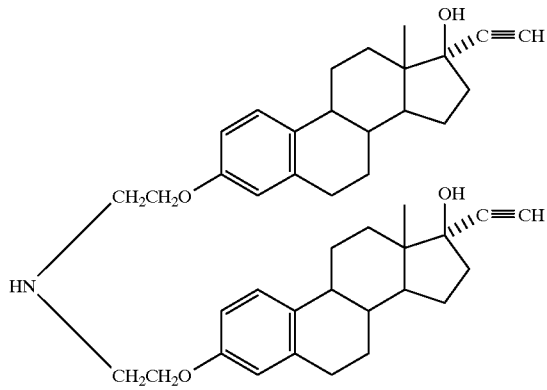

6-2. 6.6 g of the compound (6-1) described above, 0.03 g of metaformaldehyde and 20 ml of isopropanol were reacted at 60° C. for 2 hours and then 3.4 g of tetracycline was added. The reaction mixture was stirred and reacted for 8 hours. After the reaction was completed, a pale yellow solid matter (compound 6-2), i.e., bis-N,N-[17β-hydroxy-17α-ethynyl-estra-1,3,5 (10)-trien-3-oxyethyl]aminomethylene-tetracycline ($R_1=R_4=H$, $R_2=OH$, $R_3=CH_3$) was obtained in the same way as Example 1–3. The yield was 93%. m.p.= 178° C. (dec) elementary analysis: C 72.1, H 7.12, N 3.90

The structure was represented by the following molecular formula:

7-2. 3.3 g of the compound (7-2) described above, 0.03 g of metaformaldehyde and 20 ml of isopropanol were reacted at 60° C. for 2 hours and then 3.5 g of tetracycline was added. The reaction mixture was stirred and reacted for 8 hours. After the reaction was completed, a pale yellow solid matter (compound 7-2), i.e., N-[17-oxy-estra-1,3,5 (10)-trien-3-oxyethyl]-N-methylaminomethylene-tetracycline ($R_1=R_4=H$, $R_2=OH$, $R_3=CH_3$) was obtained in the same way as in Example 1–3. The yield was 90%. m.p.=190° C. (dec) elementary analysis: C 68.8, H 7.22, N 3.62

The structure was expressed by the following molecular formula:

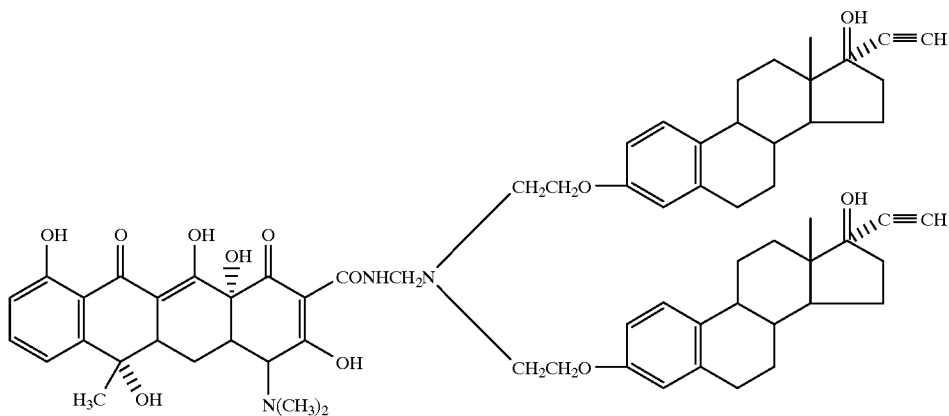

Synthesis Example 7

7-1. Synthesis of N-[17-oxy-estra-1,3,5 (10)-trien-3-oxyethyl]-N-methylamine (Compound 7-1):

2.7 g of estron, 1 g of chloroethylmethylamine and a small amount of triethylaniline were mixed with a toluene solution, and a sodium hydroxide solution was added. After the pH was adjusted to about 10, the reaction mixture was reacted for 4 hours. Thereafter, the solvent was evaporated, and the solid matter was recrystallized from alcohol to obtain a compound (7-1, $R_7=H$). The yield was 71%. m.p.= 262 to 266° C. elementary analysis: C 75.24, H 9.41, N 4.28

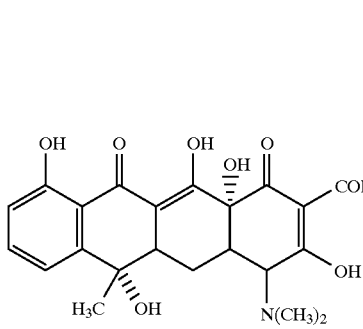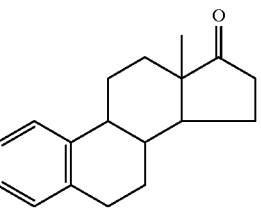

Synthesis Example 8

8-1. Synthesis of N-[3,17β-dihydroxy-estra-1,3,5 (10)-trien-6-aminoethyl]piperazine (Compound 8-1):

5.2 g of the compound (8-0) was dissolved in 120 ml of tetrahydrofuran, and 3.2 g of aminoethyl piperazine was added. The reaction mixture was subjected to turning flow and was reacted for 2 hours. THF was evaporated and removed, and 100 ml of methyl alcohol and 2.8 g of formic acid were added. Turning flow was further generated, and the reaction mixture was reacted for 3 hours. Methyl alcohol was evaporated and removed, and the residue was recrystallized from alcohol to obtain a compound 8-1. m.p.=172 to 177° C.

8-2. Synthesis of N-4-(3,17β-dihydroxy-estra-1,3,5 (10)-trien-6-aminoethyl]-piperazine-1-methylene-tetracycline (Compound 8-2):

4.1 g of the compound (8-1) described above, 0.03 g of metaformaldehyde and 20 ml of isopropanol were mixed and were reacted at 50° C. for 2 hours. After 3.5 g of tetracycline was added, the reaction mixture was stirred and reacted form 5 hours. After the reaction was completed, the reaction product was filtrated, was washed with isopropanol and ethyl ether, and was dried in vacuum to obtain a pale yellow solid matter (compound 8-2). The melting point was 167° C. (dec) and the yield was 81.2%.

and the reaction solution was neutralized by dilute acetic acid to neutrality, and was then diluted by water. After the solid matter was so formed, it was filtrated, was washed with water and was dried. The product was recrystallized from water-containing alcohol to obtain a white crystal. The melting point was 173 to 174° C. and the yield was 97.2%.

2. Preparation of 17β-estroalkynol diacetate 10 g of 17β-estroalkynol was dissolved in pyritein and 35 ml of acetic acid was placed. The reaction mixture was reacted under turning flow for one hour and was poured into ice water to form a solid matter. The resulting solid was filtrated and dried, and the reaction product was recrystallized from absolute alcohol to obtain a white crystal. The melting point was 126 to 128° C. and the yield was 97%.

3. Preparation of 6-carbonyl-17β-estroalkynol diacetate (Compound (XII))

5 g of 17β-estroalkynol diacetate was dissolved in benzene, and 0.45 g of chromium trioxide was added dropwise under the cooled state, and the mixture was then dissolved in a mixed benzene solution of 30 ml of glacial acetic acid, 20 ml of acetic acid and 30 ml of benzene. After

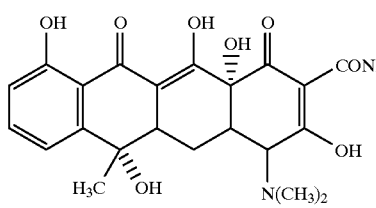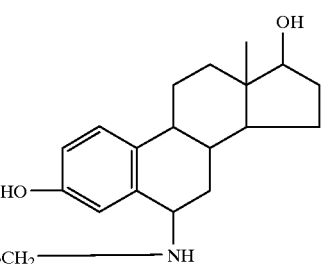

The compound (8-0) was produced in the following manner.

1. Preparation of 17β-estroalkynol 4 g of estron was dissolved in methyl alcohol, and a mixed solution of 0.8 g of potassium borohydrate, 1.76 g of sodium hydroxide and 8.8 ml of water was added dropwise at about 30° C. Thereafter, the reaction was carried out for 2 hours, the reaction was completed, the reaction solution was stirred for a while and was then poured into water. The reaction product was extracted with ethyl ether, was washed with a saturated sodium hydrogencarbonate solution, then with water, was dried and concentrated, and was thereafter separated by silica gel to obtain a product. The melting point was 173 to 175° C. and the yield was 40%.

Synthesis Example 9

Synthesis of N-4-[17-oxy-estra-1,3,5 (10)-trien-3-oxyethyl]-1-piperazine-1-methylene-doxycycline HCl (Compound 9):

2.2 g of the compound (1-2), 0.20 g of polyformaldehyde and 100 ml of isopropanol were heated and stirred at 60° C. for 1.5 hours, and 3 g of doxycycline hydrochloride was added. The reaction mixture was retained at 60° C. and was stirred for 2.5 hours. After the reaction was completed, the reaction product was filtrated, was washed with isopropanol and ethyl ether and was dried to obtain a pale yellow solid matter (compound 9) having a melting point of 172° C. (dec.). The yield was 87%.

Synthesis Example 11

Synthesis of N-4-[17-hydroxy-estra-1,3,5 (10)-trien-3-ethoxyethyl]-piperazine-1-methylene-tetracycline (Compound 11):

4.1 g of N-(17-hydroxyestron-1,3,5 (10)-trien-3-oxyethyl)piperazine, 0.5 g of polyformaldehyde and 50 ml of isopropanol were stirred at 60° C. and were reacted for 2 hours. After 4 g of tetracycline was added, the reaction mixture was retained at 40 to 45° C., and was reacted for 3 hours. The reaction product was filtrated and was washed with isopropanol and ethyl ether to obtain a pale yellow solid matter (compound 11) having a melting point of 154° C. (dec.). The yield was 68.6%.

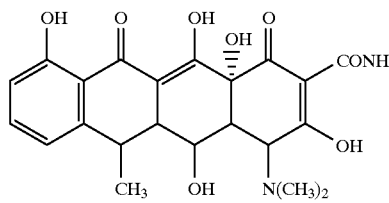
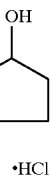

Synthesis Example 10

Synthesis of N-4-[17-oxy-estra-1,3,5 (10)-trien-3-oxyethyl]-piperazine-1-methylene-oxytetracycline (Compound 10):

0.91 g of the compound (1-2), 80 mg of polyformaldehyde and 50 ml of isopropanol were stirred and reacted at 60° C. for 2 hours. After 1.0 g of Terramycin was added, the reaction mixture was retained at 60° C. and was stirred for 3 hours. The reaction product was filtrated, was washed with isopropanol and ethyl ether and was dried to obtain a pale yellow solid matter (compound 10) having a melting point of 175° C. (dec.). The yield was 89%.

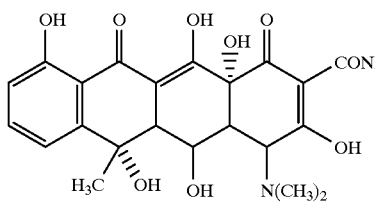
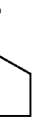

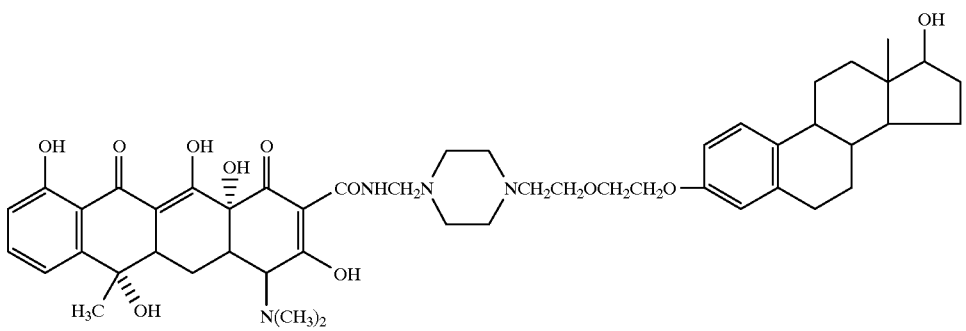

Synthesis Example 12
Synthesis of 17-hydroxy-androst-4-en-3-oxyethylaminomethylene-tetracycline:

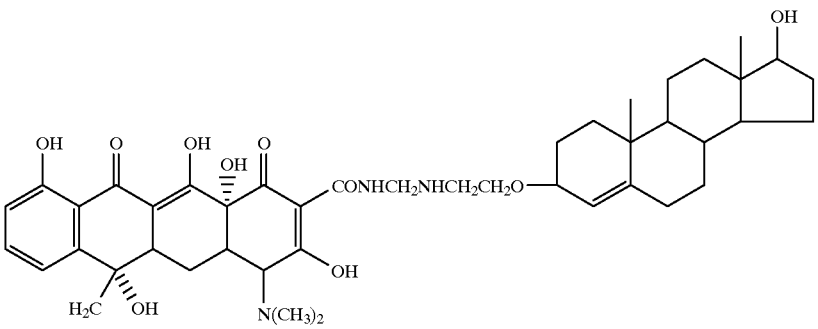

3.3 g of 3-aminoethoxy-17-hydroxy-androst-4-en, 0.3 g of metaformaldehyde and 40 ml of isopropanol were reacted at 60° C. for 4 hours. After 4.5 g of tetracycline was added, the reaction mixture was stirred and reacted for 5 hours. The reaction product was filtrated and was washed with isopropanol and ethyl ether to obtain a yellow solid matter. The yield was 92%, and the elementary analysis was as follows: C 66.78, H 7.41, N 5.38.

Synthesis Example 13
Synthesis of 17-hydroxy-androst-4-en-3-on-6-methylene-oxyethylaminomethylene-tetracycline:

3.6 g of 6-aminoethoxymethylene-17-hydroxy-androst-4-en-3-on, 0.3 g of metaformaldehyde, 4.5 g of tetracycline and 30 ml of acetone were stirred at normal temperature for 24 hours while cutting off light, and were reacted. After the reaction was completed, the reaction product was filtrated and was washed with acetone and ethyl ether to obtain a yellow solid matter. The yield was 86%, and the elementary analysis was as follows: C 67.90, H 7.67, N 5.18.

Synthesis Example 14

Synthesis of 17-hydroxy-androstan-3-oxyethylamino-methylene-tetracycline:

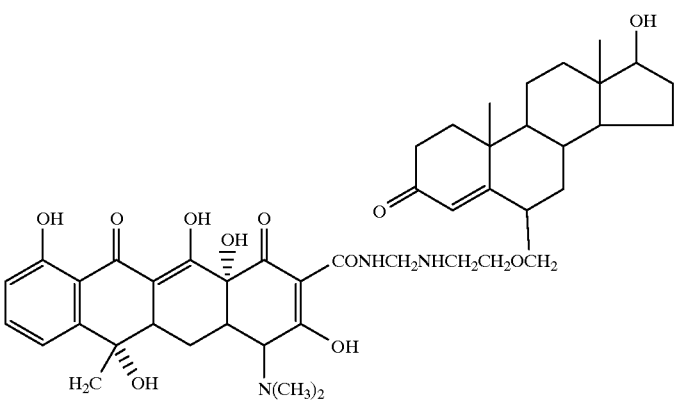

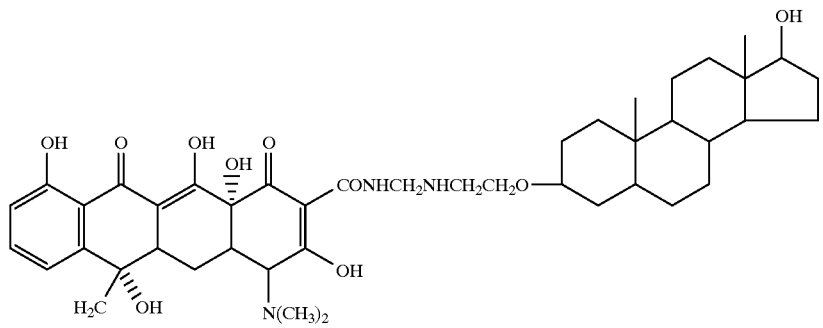

3.35 g of 3-aminoethoxy-17-hydroxy-androstan, 0.3 g of metaformaldehyde, 4.5 g of tetracycline and 30 ml of acetone were stirred and reacted at normal temperature for 30 hours while cutting off light. After the reaction was completed, the reaction product was filtrated and was washed with acetone and ethyl ether to obtain a yellow solid matter. The yield was 85%, and the elementary analysis was as follows: C 66.61, H 7.68, N 5.40.

Synthesis Example 15
Synthesis of 17β-hydroxy-18-methyl-19-norandrost-4-en-3-on-17α-butynyleneaminomethylene-tetracycline:

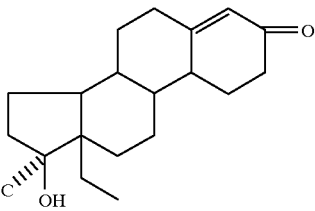

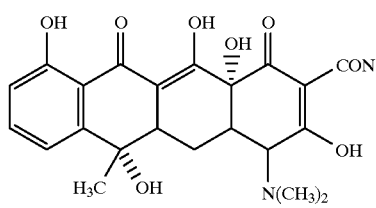

3.7 g of 17α-aminoethylethynyl-17β-hydroxy-18-methyl-19-norandrost-4-en-3-on, 0.3 g of metaformaldehyde and 30 ml of isopropanol were reacted at 60° C. for 4 hours. After 4.5 g of tetracycline was added, the reaction mixture was stirred and reacted for 6 hours. After the reaction was completed, the reaction product was filtrated and was washed with isopropanol and ethyl ether to obtain a yellow solid matter. The yield was 85% and the elementary analysis was as follows: C 68.51, H 7.11, N 5.17.

Synthesis Example 16

Synthesis of 16α, 17β-dihydroxy-estra-1,3,5 (10)-trien-3-oxyethylaminomethylene-tetracycline:

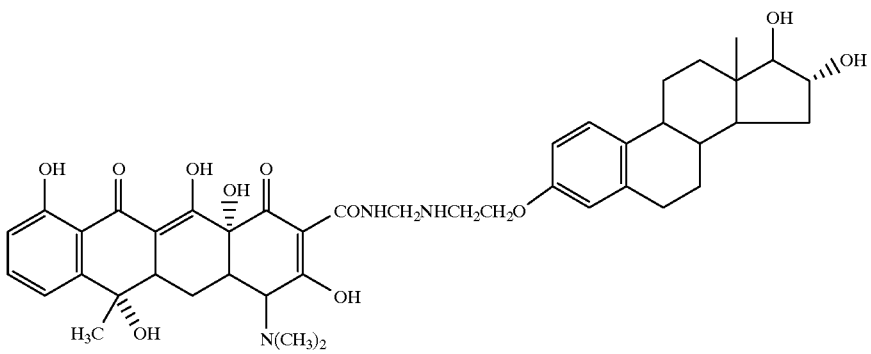

3.3 g of 3-aminoethoxy-16α, 17β-dihydroxy-estra-1,3,5 (10)-trien, 0.3 g of metaformaldehyde and 50 ml of isopropanol were reacted at 80° C. for 2 hours, and were then cooled to 40° C. After 4.5 g of tetracycline was added, the reaction mixture was reacted for 6 hours. After the reaction was completed, the reaction product was filtrated and was washed with isopropanol and ethyl ether to obtain a yellow solid matter. The yield was 85% and the elementary analysis was as follows: C 65.48; H 6.82, N 5.13.

Synthesis Example 17

Synthesis of 18-methyl-17-oxy-estra-1,3,5 (10)-trien-3-oxyethylaminomethylene-tetracycline:

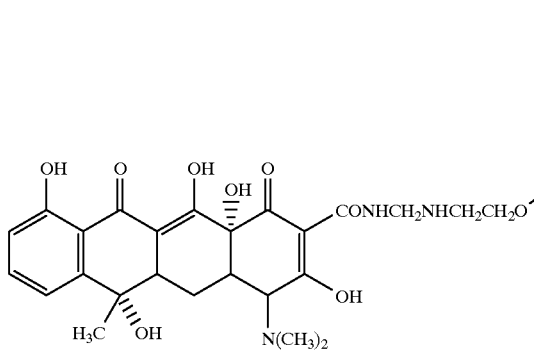

3.3 g of 3-aminoethoxy-18-methyl-estra-1,3,5 (10)-trien-17-on, 0.3 g of metaformaldehyde and 50 ml of acetone were reacted at 30° C. for 48 hours while cutting off light. After the reaction was completed, the reaction product was filtrated and was washed with isopropanol and ethyl ether to obtain a yellow solid matter. The yield was 82% and the elementary analysis was as follows: C 67.45, H 6.86, N 5.27.

Synthesis Example 18

Synthesis of 17α-hydroxy-pregna-4-en-20-on-3-oxyethylaminomethylene-tetracycline:

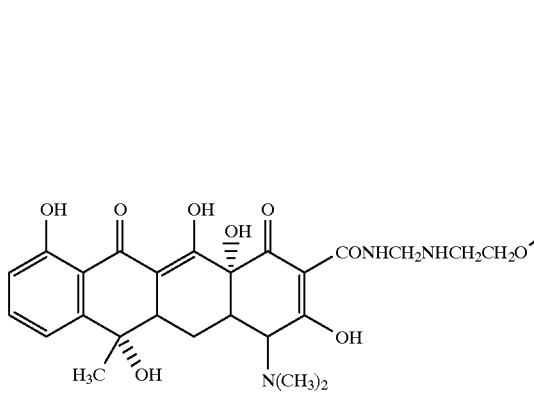

3.8 g of 3-aminoethoxy-17α-hydroxy-pregna-4-en-20-on, 0.3 g of metaformaldehyde and 50 ml of isopropanol were heated to 60° C. and reacted for 2 hours. The reaction mixture was cooled to 40° C., and 4.5 g of tetracycline was added. The reaction mixture was reacted at 60° C. for 5 hours. After the reaction was completed, the reaction product was filtrated and was washed with acetone and ethyl ether to obtain a yellow solid matter. The yield was 87% and the elementrary analysis was as follows: C 66.52, H 7.37, N 5.01.

Synthesis Example 19

Synthesis of pregna-5-en-20-on-3-oxyethylaminomethylene-tetracycline:

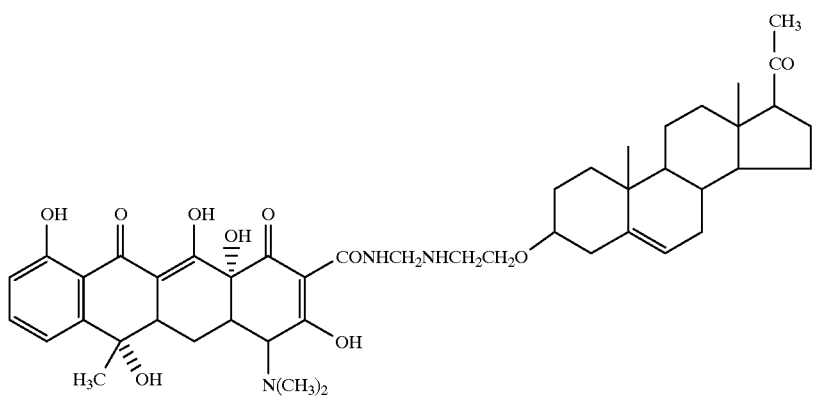

3.6 g of 3-aminoethoxy-pregna-5-en-20-on, 0.6 g of metaformaldehyde and 40 ml of isopropanol were heated to 80° C. and reacted for 2 hours. The reaction mixture was cooled to 40° C. and 4.5 g of tetracycline was added. The reaction mixture was then reacted at 4° C. for 6 hours. After the reaction was completed, the reaction product was filtrated and was washed with isopropanol and ethyl ether to obtain a solid matter. The yield was 93% and the elementary analysis was as follows: C 67.70, H 7.36, N 5.05.

Synthesis Example 20
17-hydroxy-androst-1,4-dien-3-oxyethylaminomethylene-doxycycline:

reacted at 80° C. for 2 hours. The reaction mixture was cooled to 40° C. and then 4.5 g of doxycycline hydrochloride was added. The reaction mixture was reacted for 4 hours. After the reaction was completed, the reaction product was washed with isopropanol and ethyl ether to obtain a yellow solid matter. The yield was 89% and the elementary analysis was as follows: C 67.23, H 7.25, N 5.28.

Synthesis Example 21

Synthesis of 17α-methyl-17β-hydroxy-androst-4-en-3-on-6-methyleneoxyethylaminomethylene-doxycycline:

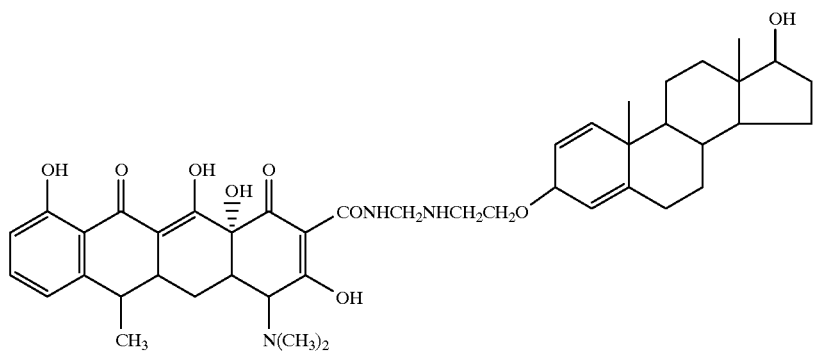

3.3 g of 3-amino-ethoxy-17β-hydroxyandrost-1,4-dien, 0.3 g of metaformaldehyde and 50 ml of isopropanol were

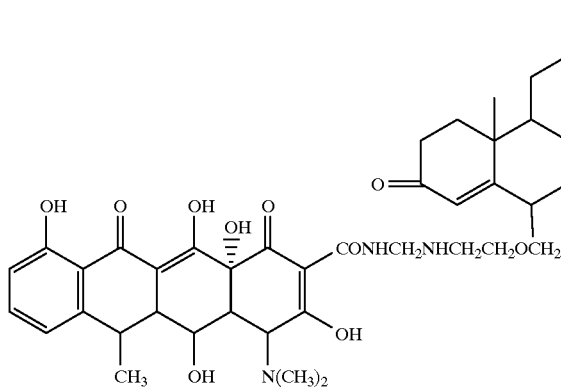

3.8 g of 6-amino-ethoxymethylene-17α-methyl-17β-hydroxy-androst-4-en-3-on, 0.3 g of metaformaldehyde and 25 ml of isopropanol were reacted at 60° C. for 4 hours. After the reaction mixture was heated and reacted, it was cooled to 40° C. and 4.5 g of doxycycline hydrochloride was added, and the reaction mixture was reacted for 8 hours. After the reaction was completed, the reaction product was washed with isopropanol and ethyl ether to obtain a yellow solid matter. The yield was 86% and the elementary analysis was as follows: C 63.62, H 7.02, N 5.13.

Synthesis Example 22
Synthesis of 17α-methyl-17β-hydroxy-androstan-3-on-2-oxyethylaminomethylene-doxycycline:

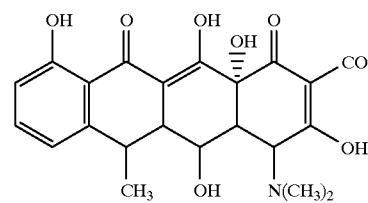 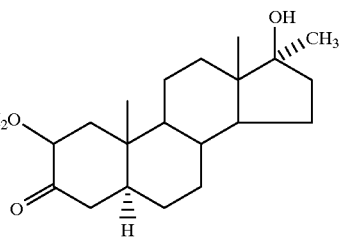

3.6 g of 2-aminoethoxy-17α-methyl-17β-hydroxy-androstan-3-on, 0.3 g of metaformaldehyde and 30 ml of isopropanol were reacted at 60° C. for 2 hours, and then 4.5 g of doxycycline hydrochloride was added. The reaction mixture was further reacted. After the reaction was completed, the reaction product was washed with isopropanol and ethyl ether to obtain a yellow solid matter. The yield was 91% and the elementary analysis was as follows: C 65.91, H 7.51, N 5.07.

Synthesis Example 23

Synthesis of 17α-methyl-17β-hydroxy-19-norandrost-4-en-3-on-6-methyleneoxyethylamino-doxycycline:

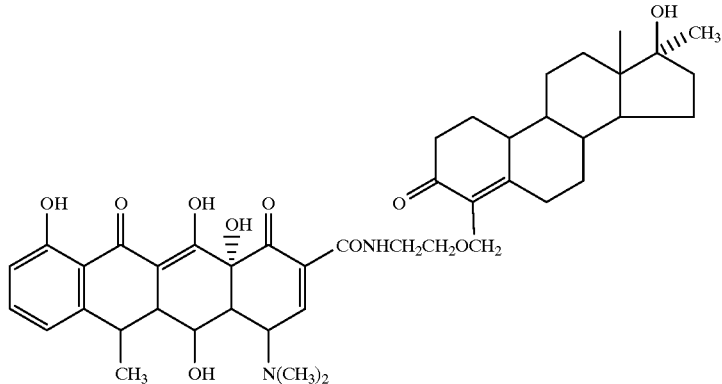

3.7 g of 6-aminoethoxymethylene-17α-methyl-17β-hydroxy-19-nor-androst-4-en-3-on, 0.3 g of metaformaldehyde and 50 ml of acetone were reacted at 30° C. for 2 hours, and 4.5 g of doxycycline hydrochloride was added. The reaction mixture was further reacted for 30 hours. After the reaction was completed, the reaction product was filtrated and was washed with isopropanol and ethyl ether to obtain a yellow solid matter. The yield was 87% and the elementary analysis was as follows: C 63.64, H 7.03, N 5.18.

Synthesis Example 24
Synthesis of 17α-ethynyl-17β-hydroxy-androst-5-(10)-en-3-on-6-methyleneoxyethylaminomethylene-doxycycline:

androst-4,9-dien-3-on, 0.3 g of metaformaldehyde and 40 ml of isopropanol were heated and reacted at 80° C. for 2 hours. After the reaction mixture was cooled to 40° C., 4.5 g of doxycycline hydrochloride was added and reaction mixture was reacted for 6 hours. After the reaction was completed, the reaction product was filtrated and was washed with isopropanol and ethyl ether to obtain a yellow solid matter. The yield was 90% and the elementary analysis was as follows: C 68.76, H 6.88, N 5.72.

Synthesis Example 2
Synthesis of 16,17-isopropylidene-16,17-dioxyestra-1,3,5(10)-trien-3-oxyethylaminomethylene-doxycycline:

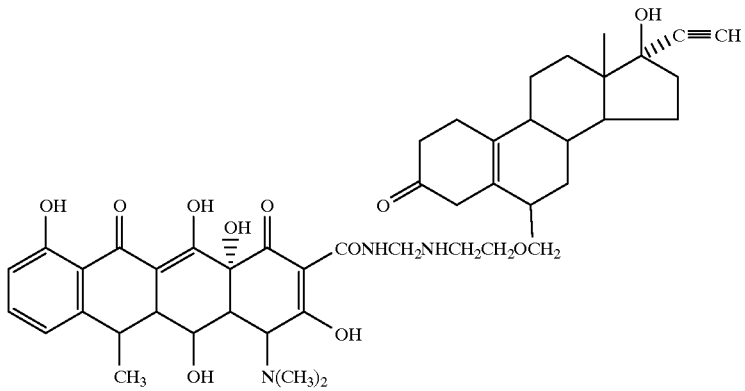

3.7 g of 6-amino-ethoxymethylene-17α-ethynyl-17β-hydroxy-androst-5-(10)-en-3-on, 0.3 g of metaformaldehyde and 50 ml of isopropanol were reacted at 60° C. for 2 hours, and 4.5 g of doxycycline hydrochloride was added. The reaction mixture was reacted at 40° C. for 8 hours. After the reaction was completed, the reaction product was filtrated and was washed with isopropanol and ethyl ether to obtain a yellow solid matter. The yield was 87% and the elementary analysis was as follows: C 66.81, H 7.06, N 5.01.

Synthesis Example 25
17α-propylene-17β-hydroxy-11-dimethylaminophenyl-androst-4,9-dien-3-on-6-methyleneoxyethylaminomethylene-doxycycline:

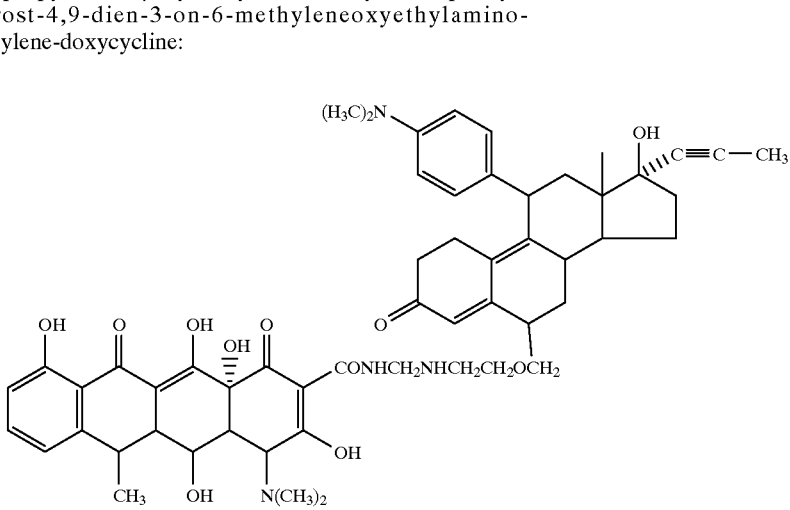

5 g of 6-amino-ethoxymethylene-11-(4'-dimethylaminophenyl)-17α-propylene-17β-hydroxy-

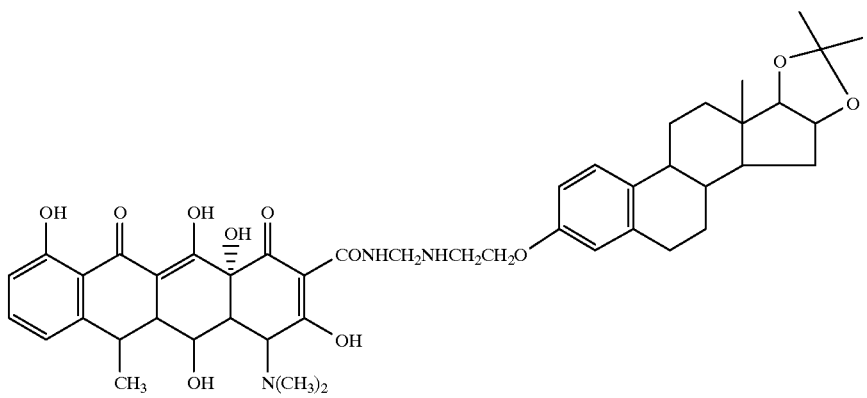

3.7 g of 16,17-isopropylidene-16,17-dioxy-estra-1,3,5 (10)-trien-3-aminoethyl ether, 0.3 g of metaformaldehyde and 50 ml of isopropanol were reacted at 60° C. for 2 hours, and 4.5 g of doxycycline hydrochloride was added. The reaction mixture was further reacted for 8 hours. After the reaction was completed, the reaction product was filtrated and was washed with isopropanol and ethyl ether to obtain a yellow solid matter. The yield was 95% and the elementary analysis was as follows: C 66.61, H 6.90, N 5.18.

Synthesis Example 27

Synthesis of 3,17-dihydroxy-estra-1,3,5 (10)-trien-17-acetate-7-methyleneoxyethylaminomethylene-doxycycline:

were reacted at 60° C. for 4 hours, and 4.5 g of doxycycline hydrochloride was added. The reaction mixture was further reacted for 4 hours. After the reaction was completed, the reaction product was filtrated and was washed with isopropanol and ethyl ether to obtain a yellow solid matter. The yield was 88% and the elementary analysis was as follows: C 65.34, H 6.68, N 4.95.

Synthesis Example 28

Synthesis of 17-hydroxy-pregna-4-en-20-on-3-oxyethylaminomethylene-doxycycline:

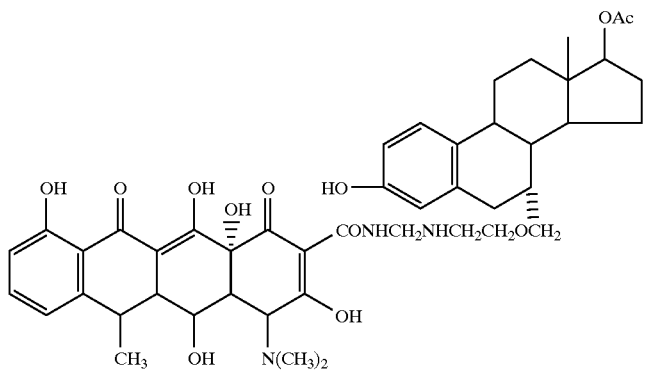

33.8 g of 7-aminoethyloxymethylene-estra-3,17-dien-17-acetate, 0.3 g of metaformaldehyde and 50 ml of isopropanol

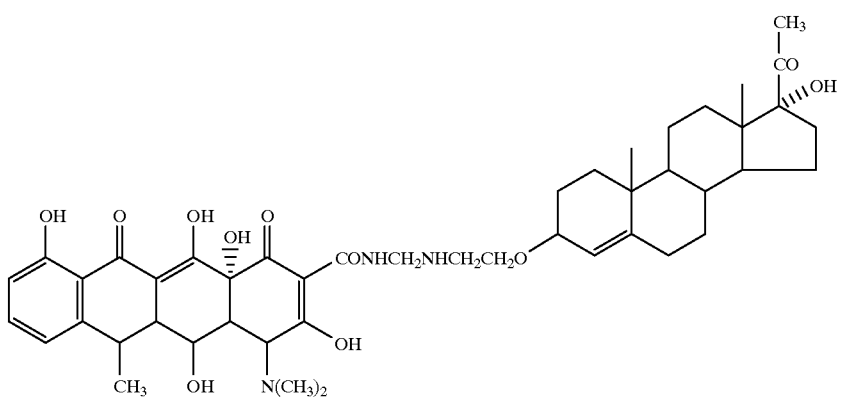

3.7 g of 3-aminoethyoxy-17α-hydroxypregna-4-en-20-on, 0.3 g of metaformaldehyde and 40 ml of isopropanol were heated and reacted at 60° C. for 2 hours, and 4.5 g of doxycycline hydrochloride was added. The reaction mixture was further reacted for 4 hours. After the reaction was completed, the reaction product was filtrated and was washed with isopropanol and ethyl ether to obtain a yellow solid matter. The yield was 92% and the elementary analysis was as follows: C 66.41, H 7.40, N5.14.

Synthesis Example 29
Synthesis of pregna-4-en-3,20-dion-6-methyleneoxy-ethylaminomethylene-doxycycline:

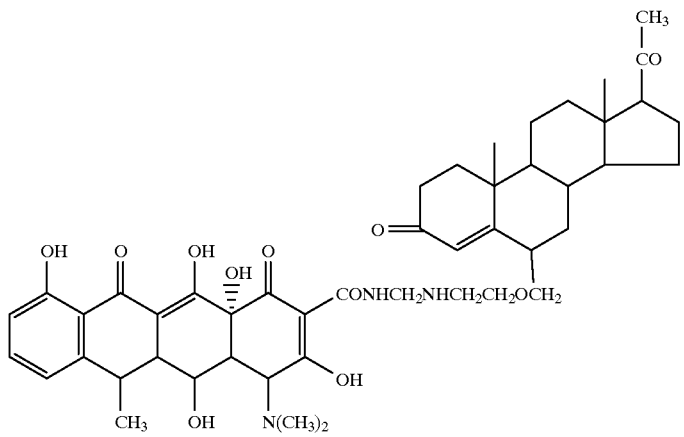

3.9 g of 6-aminoethoxymethylene-pregna-4-en-3,20-dion, 0.3 g of metaformaldehyde and 50 ml of isopropanol were reacted at 60° C. for 3 hours and 4.5 g of doxycycline hydrochloride was added. The reaction mixture was further reacted for 4 hours. After the reaction was completed, the reaction mixture was further reacted for 4 hours. After the reaction was completed, the reaction product was filtrated and was washed with isopropanol and ethyl ether to obtain a yellow solid matter. The yield was 93% and the elementary analysis was as follows: C 67.77, H 7.36, N 4.59.

Synthesis Example 30
Synthesis of 3,17-dihydroxy-estra-1,3,5 (10)-trien-11-(4-phenoxy-ethylamino)-methylene-doxycycline:

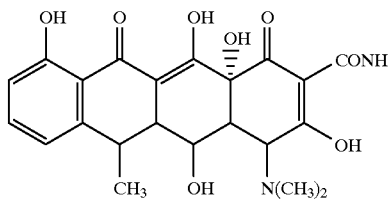
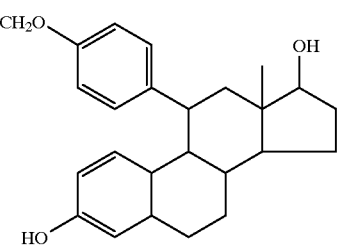

4 g of 11-(4'-aminoethoxyphenyl)-3,17-dihydroxy-estra-1,3,5 (10)-trien, 0.3 g of metaformaldehyde and 50 ml of isopropanol were reacted at 60° C. for 2 hours and 4.5 g of doxycycline hydrochloride was added. The reaction mixture was further reacted for 8 hours. After the reaction was completed, the reaction product was filtrated and was washed with isopropanol and ethyl ether to obtain a yellow solid matter. The yield was 89% and the elementary analysis was as follows: C 68.13, H 6.69, N 4.73.

Synthesis Example 31
Synthesis of 17β-hydroxy-17α-methyl-andrstano-(3,2-C)-pyrazol-N-methylene-tetracycline:

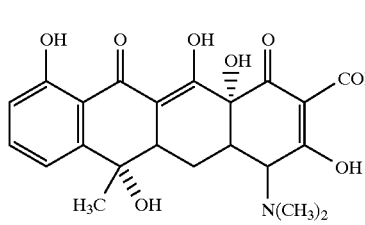

3.29 g of 17β-hydroxy-17α-methyl-androstano-(3,2-C)-pyrazol, 0.3 g of metaformaldehyde and 30 ml of isopropanol were reacted at 40° C. for 2 hours and 4.5 g of tetracycline. The reaction mixture was stirred and reacted for 6 hours. After the reaction was completed, the reaction product was filtrated and was washed with isopropanol and ethyl ether to obtain a yellow solid matter. The yield was 89% and the elementary analysis: was as follows: C 67.48, H 7.07, N 7.30.

Experiment 1: Intracorporeal Distribution of Compound

The compound 1-3 produced in Synthesis Example 1–3 was subjected to radioactive labelling by $^3H$ (0.34 mCi/mg), and was injected into the vein of the tail of mice in a dosage of 20 μCi/20 g. Groups of mice each comprising five mice were killed at 1 minute, 5 minutes, 15 minutes, 30 minutes, 1 hour, 4 hours, 6 hours, 24 hours, 48 hours and 72 hours after the injection, and 50 μl of the blood was collected from the eye socket of each mouser. Further, the heart, the womb, the small intestine, bones (thighbone), etc., were collected from each mouse, and 50 mg of the tissue (50 μl for the blood) was placed into a plastic test tube. Further, 0.2 ml of perchloric acid, 0.4 ml of hydrogen peroxide and a drop of n-octyl alcohol were put into the test tube, and the test tube was left in a water bath at 75° C. for 45 minutes. Next, 0.1 ml of this digestive fluid was sampled and was placed into a bottle storing a scintillating solution and furthermore, 5 ml of 0.5% scintillating solution was mixed. After the solution became transparent, it was placed into an FJ2105 liquid scintillation counter so as to measure radioactivity and to determine cpm of the sample. Separately, dpm of 52 samples obtained from four groups of animals was measured (External Standard Method).

The quantity of the drug inside the tissue was determined in the following way.

Drug quantity in tissue (cpm/mg)=(sample cpm)÷(digested tissue quantity (mg))

Drug quantity in tissue (μg/mg)=(sample cpm/mg×6)÷(count efficiency (E)×2.22×10$^{7\times 0.34}$ mCi/mg (specific radioactivity))

The results were as follows.

TABLE 1

Change of drug concentration in blood (mean value of 5 animals at each time)
Change of drug concentration in blood (cpm/50 μl after intravenous injection of $^3$H— compound 1-3.

| time after injection | 1 min. | 5 min. | 15 min. | 30 min. | 1 hr. | 4 hr. | 6 hr. | 24 hr. | 48 hr | 72 hr |
|---|---|---|---|---|---|---|---|---|---|---|
| cpm | 8665 | 5238 | 2638 | 2347 | 952 | 659 | 715 | 523 | 272 | 190 |
| SD | ±1700 | ±2263 | ±941 | ±452 | ±88 | ±60 | ±57 | ±102 | ±40 | ±25 |

TABLE 2

Change of drug quantity in tissue (cpm/mg tissue)

| hour | heart | ovary | womb | muscle | brain | stomach | intestines | bone |
|---|---|---|---|---|---|---|---|---|
| 1' | 40 | 40 | 28 | 28 | 20 | 30 | 53 | 38 |
| 5' | 43 | 48 | 37 | 32 | 13 | 39 | 138 | 32 |
| 15' | 38 | 37 | 24 | 15 | 9 | 28 | 85 | 23 |
| 30' | 37 | 41 | 30 | 22 | 10 | 32 | 150 | 23 |
| 1° | 13 | 19 | 12 | 11 | 7 | 12 | 28 | 15 |
| 4° | 8 | 15 | 7 | 7 | 7 | 10 | 13 | 11 |
| 6° | 10 | 17 | 9 | 6 | 6 | 12 | 9 | |
| 24° | 8 | 7 | 4 | 4 | 4 | 6 | 6 | 9 |
| 48° | 4 | 7 | 4 | 5 | 4 | 4 | 4 | 6 |
| 72° | 4 | 6 | 4 | 4 | 3 | 3 | 3 | 5 |

*Mean value of five animals

TABLE 3

Change of drug quantity in tissue: (μg/mg tissue)

| hour | heart | ovary | womb | intestines | bone |
|---|---|---|---|---|---|
| 1' | 0.834 | 0.822 | 0.588 | 1.104 | 0.780 |
| 5' | 0.894 | 0.99 | 0.774 | 2.874 | 0.654 |
| 15' | 0.792 | 0.762 | 0.204 | 1.770 | 0.468 |
| 30' | 0.270 | 0.846 | 0.624 | 3.126 | 0.468 |
| 1° | 0.270 | 0.390 | 0.252 | 0.582 | 0.306 |
| 4° | 0.168 | 0.306 | 0.144 | 0.270 | 0.228 |
| 6° | 0.210 | 0.348 | 0.186 | 0.252 | 0.186 |
| 24° | 0.168 | 0.150 | 0.084 | 0.126 | 0.186 |
| 48° | 0.084 | 0.150 | 0.084 | 0.084 | 0.126 |
| 72° | 0.084 | 0.126 | 0.084 | 0.066 | 0.102 |

*Mean value of five animals

Experiment 2: Acute Toxicity Test (1) Sample:

The compound 1-3 was pale yellow crystalline powder and its lot number was 930113. The solution was a pale yellow transparent solution, and has a concentration of 50 mg/ml and a pH of about 5. It was offered from Osteoporosis Research Laboratory, Department of Pharmacy, West China University of Medical Science School (WCUMS).

(2) Animals:

Kunming species mice, health: first class, weight: 18 to 21 g, half male and half female. The mice were offered from Experimental Animal Center of WCUSM.

(3) Measurement of half lethal dose ($LD_{50}$):

Four to five dose groups were prepared in equal ratios (1:0.7 to 0.8) within the LD range of 0 to 100% obtained by preliminary tests. The drug for peroral administration was prepared by suspending the solid compound 1-3 in 1% $CMCNa_2$ to form a suspension. For injection, drug solutions having different concentrations were prepared by dissolving the compound 1-3 in physiological saline solution by a low specific gravity dilution method. The animals were starved (but without limiting water), and 20 hours later, ten mice were grouped at random into each group irrespective of their sex and body weight. The drug was dosed once a day in a dose of 0.2 ml/10 g and the animals were inspected. Dead animals were dissected and any change of the morbid state was examined with by the naked eye.

(4) Test Results:

(a) Measurement of maximum tolerance dose of compound 1-3 to mice:

Maximum tolerance dose when no death was observed at the time of preliminary tests was measured. After the chemical was dosed once in the maximum concentration and in the maximum capacity for peroral administration to 20 mice (10 males and 10 females), the animals were examined for 7 days. As a result, no abnormality was found in the mice and no mouse was dead, either. The maximum tolerance dose (MTD) was >6 g/kg.

(b) The results after the compound 1-3 was injected to the vein of the tail of the mice were as follows.

TABLE 4

| Test sample dosage (mg/kg) | logarithmic dosage (X) | No. of animals | No. of dead animals | death ratio (%) | provit unit (Y) |
|---|---|---|---|---|---|
| 250 | 2.3979 | 10 | 10 | 100 | |
| 200 | 2.3010 | 10 | 10 | 100 | 7.40 |
| 160 | 2.2041 | 10 | 8 | 80 | 5.84 |
| 128 | 2.1072 | 10 | 2 | 20 | 4.16 |
| 102.4 | 2.0103 | 10 | 0 | 0 | 2.60 |

Calculation processing: by Bliss method
$LD_{50}$ = 143.11 mg/kg
$LD_{50}$; inside range of 95% reliability limit: 132.95 to 154.05 mg/kg (5) Conclusion:

The maximum tolerance dose (MTD) of compound 1–3 for single administration to the mice was at least 6 g/kg and its toxicity was extremely low. The $LD_{60}$ for the intravenous injection to the vein of the tail of the mice was 143.11 mg/kg. After intravenous injection, activity of the mice decreased and then the mice started jumping and went into spasm. The eyeball protruded and changed to white, and incontinence of urine and feces was observed. Although the major proportion of the poisoned animals died instantly, an extremely few survived were also dead within 24 hours. Those survived for more than 24 hours were not killed within 7 days. No difference was found between the sexes of the dead animals, and any change of the morbid state could not at all be observed by the naked eye in the dissection of the dead animals. The room temperature of the testing room was 17° C.

Experiment 3: Osteogenesis Test (1)

A first generation incubation system of the osteoblast originating from the calvaria of Whister rats (female, 6-months' age) was used as the test cells. After the start of incubation, the sample drug (compound 1-3) was added once a day to the medium in a dose of $10^{-6}$M, $10^{-8}$M or $10^{-9}$M on the second and third days (propagation period). Alternatively, the compound 1-3 in the amount described above was added once a day to the medium for 4 days (calcification period) from the seventh day from the start of incubation. On the fourteenth day from the start of incubation, the cells were subjected to von Kossa dyeing and detection of phosphates was carried out. The area of the bone knots which were dyed to brown was confirmed by the naked eye and was used as the index for osteogenesis. The results were as follows.

TABLE 5

Osteogenesis promotion function of compound 1–3

| addition concentration (M) | propagation period | calcification period |
|---|---|---|
| $10^{-9}$ | → | ↑ |
| $10^{-8}$ | → | ↑↑ |
| $10^{-6}$ | → | ↑ |

Figure 1B:
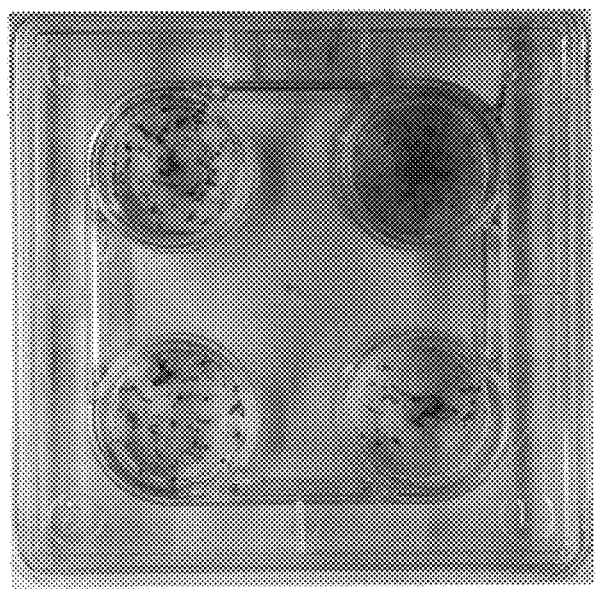
Figure 2A:
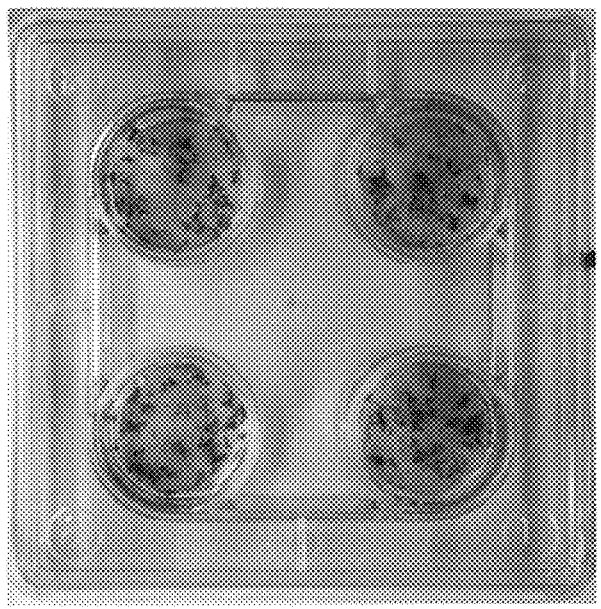
FIG. 2 is a photograph showing the result of Experiment No. 3.
Figure 2B:
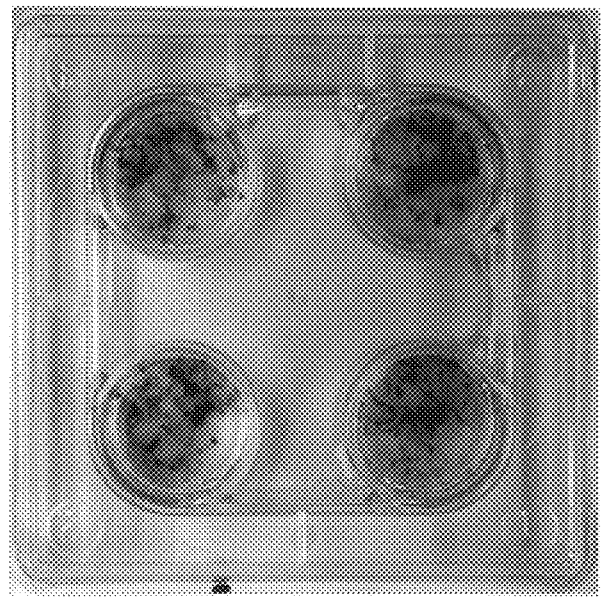
Figure 2C:
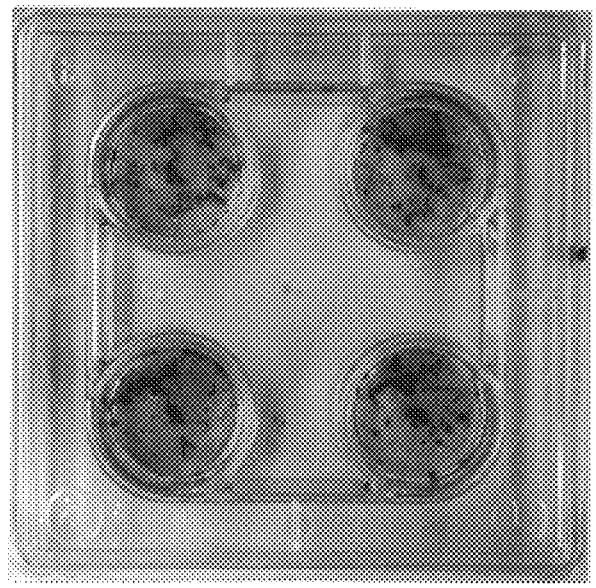
Figure 2D:
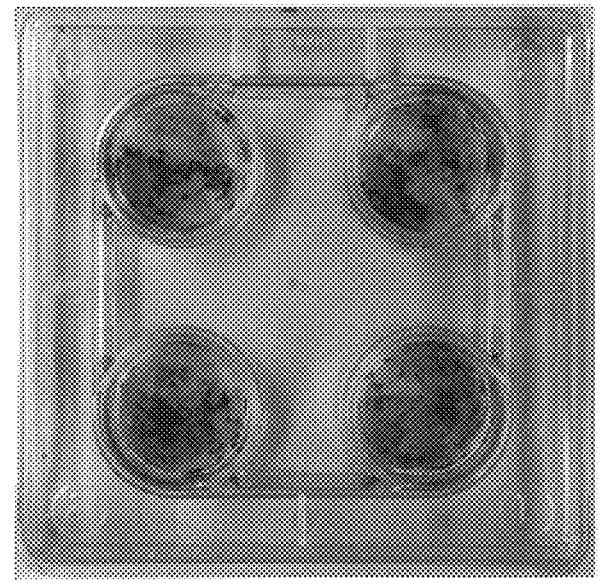
Figure 3A:
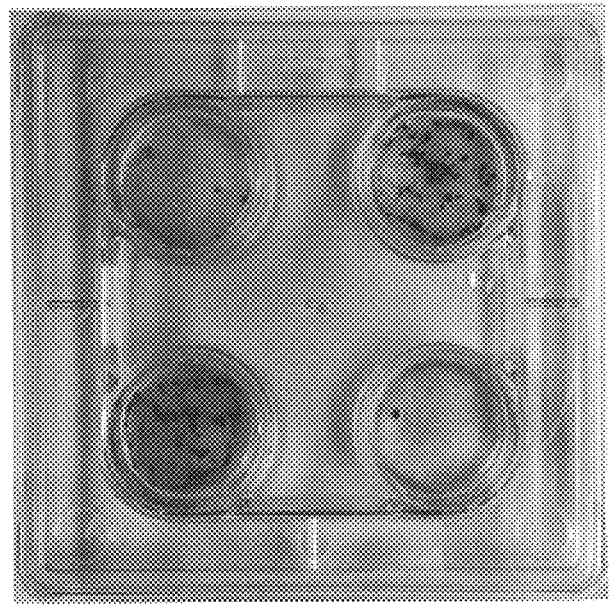
FIG. 3 is a photograph showing the result of Experiment No. 3.
Figure 3B:
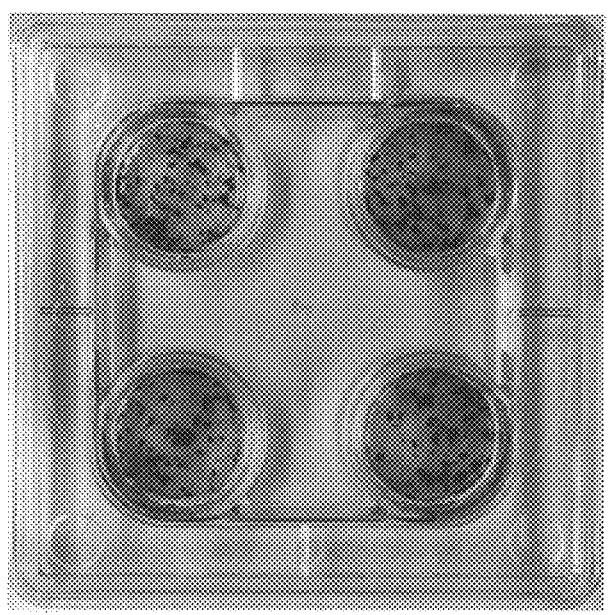
Figure 3C:
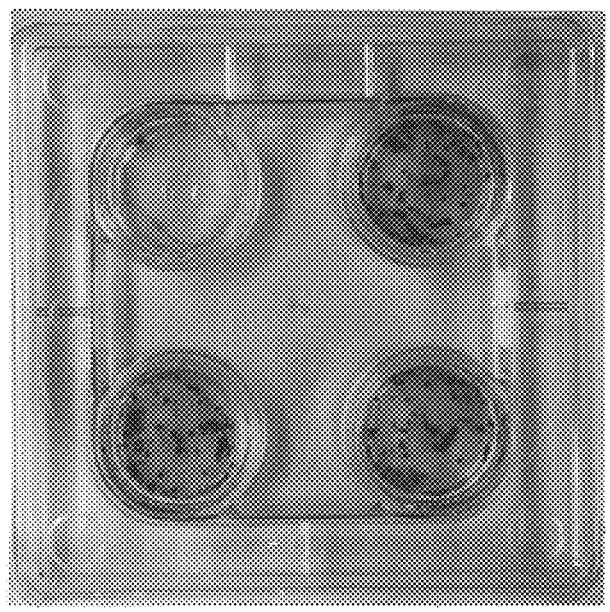
Figure 3D:
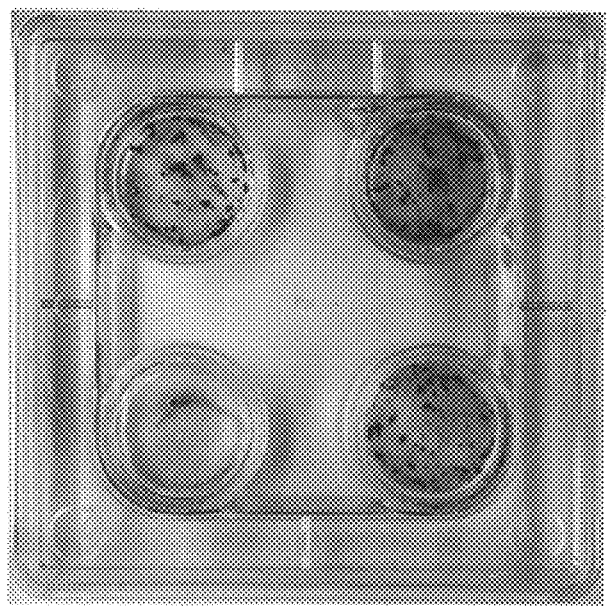

*Transverse arrow indicates that osteogenesis did not exist and upward arrow indicates promotion of osteogenesis FIGS. 1 to 3 show the results when the same procedure described above was repeated three times. In the drawings, symbol A represents no addition of the drug, B represents addition in $10^{-9}$M, C represents addition in $10^{-8}$M and D represents addition in $10^{-6}$M.

As is obvious from the results described above, the compound of the present invention exhibited the osteogenesis promotion; function.

Experiment 4: Osteogenesis Experiment 2

A first generation incubation system of the marrow cells originating from the thighbones of Whister rats (female, 6-months' age) were used as the cells for the experiments, and the compound 1-3 was added once a day in an amount of $10^{-8}$M or $10^{-6}$M to the medium on the seventh, ninth and eleventh days from the start of incubation (calcification period). Evaluation was carried out in the same way as in Experiment 3. The results were tabulated in the following table.

TABLE 6

Osteogenesis promotion function of Compound 1–3

| addition quantity | Osteogenesis promotion |
|---|---|
| $10^{-8}$ | ↑ |
| $10^{-6}$ | → |

As is obvious from the table given above, the compound of the present invention exhibited the osteogenesis promotion function.

We claim:

1. A compound represented by the following formula (I):

$$X—Y—Z \qquad (I)$$

wherein X is a monovalent group represented by the following formula (II):

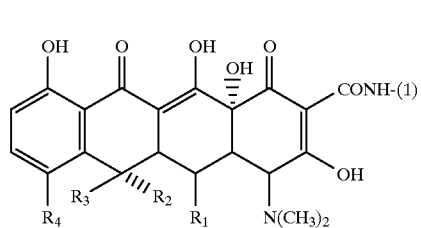

(II)

wherein $R_1$ is hydrogen or a hydroxyl group, $R_2$ is hydrogen or a hydroxyl group, $R_3$ is hydrogen or a methyl group and $R_4$ is hydrogen, halogen or a dimethylamino group;

Y is a divalent group represented by the following formula (IV) or (V):

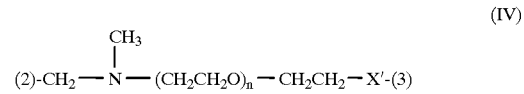

(IV)

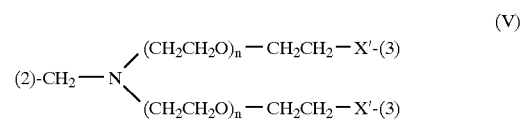

(V)

wherein n is 0 to 4, and —X'— is a direct bond, —O— or —NH—; and

Z is a monovalent group formed by removing a hydrogen atom or a hydroxyl group from a compound represented by the following formula (VI):

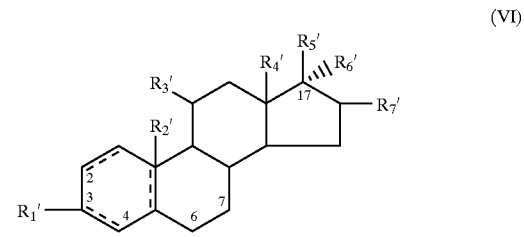

(VI)

wherein $R_1'$ is HO— or O═; $R_2'$ is a hydrogen atom or a methyl group; $R_3'$ is a hydrogen atom, a phenyl group or a substituted phenyl group; $R_4'$ is a methyl group or an ethyl group; $R_5'$ is a hydroxyl group, a ketone group or an acetyl group; $R_6'$ is hydrogen, a hydroxyl group, a methyl group, an ethynyl group or a propynyl group; or $R_5'$ and $R_6'$ together form ═O; $R_7'$ is hydrogen, a hydroxyl group or ═O, or $R_6'$ and $R_7'$ are together bonded to oxygen atoms of a 2,2-dioxypropyl group; and the symbol $\overline{...}$ represents a single bond or a double bond; whereby this bond group exists at the 2-position, 3-position, 4-position, 6-position, 7-position or 17-position, or at the phenyl group bonded to the 11-position, (1) of the formula (II) and (2) of the formulas (IV) and (V) are directly bonded, and (3) of the formulas (IV) and (V) and any of the bond groups of the formula (VI) are directly bonded.

2. A compound according to claim 1, wherein said monovalent group represented by the formula (II) is a monovalent group of a tetracycline compound wherein $R_1$ is hydrogen, $R_2$ is hydroxyl group, $R_3$ is a methyl group and $R_4$ is hydrogen.

3. A compound according to claim 1, wherein said monovalent group represented by the formula (II) is a monovalent group of Terramycin wherein $R_1$ is a hydroxyl group, $R_2$ is a hydroxyl group, $R_3$ is a methyl group and $R_4$ is methyl.

4. A compound according to claim 1, wherein said monovalent group represented by the formula (II) is a monovalent group of chlorotetracycline wherein $R_1$ is hydrogen, $R_2$ is a hydroxyl group, $R_3$ is a methyl group and $R_4$ is chlorine.

5. A compound according to claim 1, wherein said monovalent group represented by the formula (II) is a monovalent group of deoxytetracycline wherein $R_1$ is a hydroxyl group, $R_2$ is hydrogen, $R_3$ is a methyl group and $R_4$ is hydrogen.

6. A compound according to claim 1, wherein said monovalent group represented by the formula (II) is a monovalent group of aminotetracycline wherein $R_1$ is hydrogen, $R_2$ is hydrogen, $R_3$ is hydrogen and $R_4$ is dimethylamino group.

7. A compound according to claim 1, wherein said monovalent group represented by the formula (VI) is a monovalent group of estron wherein $R_5'$ and $R_6'$ together form $=O$ and $R_7'$ is hydrogen.

8. A compound according to claim 1, wherein said monovalent group represented by the formula (VI) is a monovalent group of estradiol wherein $R_5'$ is a hydroxyl group, $R_6'$ is hydrogen and $R_7'$ is hydrogen.

9. A compound according to claim 1, wherein said monovalent group represented by the formula (VI) is a monovalent group of estroalkynol wherein $R_5'$ is a hydroxyl group, $R_6'$ is an ethyryl group and $R_7'$ is hydrogen.

10. A compound according to claim 1, wherein said monovalent group represented by the formula (VI) is a monovalent group of estriol wherein $R_5'$ is a hydroxyl group, $R_6'$ is hydrogen and $R_7'$ is a hydroxyl group.

* * * * *

UNITED STATES PATENT AND TRADEMARK OFFICE
CERTIFICATE OF CORRECTION

PATENT NO. : 6,028,207
DATED : February 22, 2000
INVENTOR(S) : Hu ZHENG *et al.*

It is certified that error appears in the above-identified patent and that said Letters Patent is hereby corrected as shown below:

On the title page, under "Related U.S. Application Data" please add
--[62] Division of application No. 08/338,505, Mar. 1, 1995, Pat. No. 5,760,214, which is a National Stage application of PCT/JP94/00489 filed on Mar. 25, 1994.--

Please add under "Foreign Application Priority Data"

--[30] Foreign Application Priority Data
March 25, 1993     [CN]    China ......................93 1 10919.1
December 29, 1993 [JP]    Japan ......................5-355404--.

Signed and Sealed this

Sixth Day of March, 2001

*Attest:*

NICHOLAS P. GODICI

*Attesting Officer*     *Acting Director of the United States Patent and Trademark Office*